(12) United States Patent
Stone et al.

(10) Patent No.: US 8,303,604 B2
(45) Date of Patent: Nov. 6, 2012

(54) SOFT TISSUE REPAIR DEVICE AND METHOD

(75) Inventors: Kevin T. Stone, Winona Lake, IN (US); Nathan M. Sautter, North Manchester, IN (US); Brian K. Berelsman, Warsaw, IN (US); Jeffery D. Arnett, Gilbert, AZ (US); Joshua A. Butters, Chandler, AZ (US); Dylan M. Hushka, Chandler, AZ (US); Nicholas R. Slater, Chandler, AZ (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 348 days.

(21) Appl. No.: 12/570,854

(22) Filed: Sep. 30, 2009

(65) Prior Publication Data

US 2010/0087857 A1  Apr. 8, 2010

Related U.S. Application Data

(63) Continuation-in-part of application No. 12/489,181, filed on Jun. 22, 2009, which is a continuation-in-part of application No. 12/474,802, filed on May 29, 2009, now Pat. No. 8,088,130, which is a continuation-in-part of application No. 11/541,505, filed on Sep. 29, 2006, now Pat. No. 7,658,751, and a (Continued)

(51) Int. Cl.
*A61B 17/10* (2006.01)

(52) U.S. Cl. .......................................... 606/139

(58) Field of Classification Search .................. 606/139, 606/142, 143, 219; 227/175.1, 175.2, 176.1
See application file for complete search history.

(56) References Cited

U.S. PATENT DOCUMENTS 65,499 A  6/1867  Miller
(Continued)

FOREIGN PATENT DOCUMENTS

AU  4957264  3/1966
(Continued)

OTHER PUBLICATIONS

"AperFix® System Surgical Technique Guide. Single Tunnel Double Bundle. ™" Cayenne Medical brochure. (Aug. 2008) 8 sheets.

(Continued)

*Primary Examiner* — Dianne Dornbusch
(74) *Attorney, Agent, or Firm* — Harness, Dickey

(57) ABSTRACT

A soft tissue repair device can include a housing having a handle, a deployment system having an actuation member, and an insertion system having an inserter and a slider. The slider can be coupled to the actuation member and movable relative to the inserter between deployed and retracted positions. First and second anchors can be carried on an external surface of the slider such that the anchors are spaced apart and portions of the anchors are coaxial with the slider and each other. A flexible strand can couple the anchors. The insertion system can cooperate with the deployment system to move the slider to the deployed position to deploy the first anchor upon activating the actuation member a first time, and to move the slider to the deployed position from the retracted position to deploy the second anchor upon actuating the actuation member a second time after the first time.

33 Claims, 19 Drawing Sheets

Related U.S. Application Data continuation-in-part of application No. 11/541,506, filed on Sep. 29, 2006, now Pat. No. 7,601,165, application No. 12/570,854, which is a continuation-in-part of application No. 12/014,399, filed on Jan. 15, 2008, now Pat. No. 7,909,851, application No. 12/570,854, which is a continuation-in-part of application No. 12/014,340, filed on Jan. 15, 2008, now Pat. No. 7,905,904, which is a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, which is a continuation-in-part of application No. 11/408,282, filed on Apr. 20, 2006, now abandoned, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned, which is a continuation-in-part of application No. 10/983,236, filed on Nov. 5, 2004, now abandoned, application No. 12/570,854, which is a continuation-in-part of application No. 12/489,168, filed on Jun. 22, 2009, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836.

(60) Provisional application No. 60/885,062, filed on Jan. 16, 2007, provisional application No. 60/885,057, filed on Jan. 16, 2007.

(56) References Cited

U.S. PATENT DOCUMENTS

| | | | |
|---|---|---|---|
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 417,805 | A | 12/1889 | Beaman |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| RE26,501 | E | 12/1968 | Kendrick et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,547,389 | A | 12/1970 | Mitchell |
| 3,579,831 | A | 5/1971 | Stevens et al. |
| 3,590,616 | A | 7/1971 | Schussler |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |

| Patent No. | Date | Inventor |
|---|---|---|
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |

| | | | | | | |
|---|---|---|---|---|---|---|
| 4,851,005 A | 7/1989 | Hunt et al. | | 5,154,189 A | 10/1992 | Oberlander |
| 4,858,608 A | 8/1989 | McQuilkin et al. | | 5,156,616 A | 10/1992 | Meadows et al. |
| 4,860,513 A | 8/1989 | Whitman | | 5,163,960 A | 11/1992 | Bonutti |
| 4,863,383 A | 9/1989 | Grafelmann et al. | | D331,626 S | 12/1992 | Hayhurst et al. |
| 4,870,957 A | 10/1989 | Goble et al. | | 5,169,400 A | 12/1992 | Muhling et al. |
| 4,873,976 A | 10/1989 | Schreiber | | 5,176,682 A | 1/1993 | Chow |
| 4,887,601 A | 12/1989 | Richards | | 5,178,629 A | 1/1993 | Kammerer |
| 4,890,615 A | 1/1990 | Caspari et al. | | 5,183,458 A | 2/1993 | Marx |
| 4,893,619 A | 1/1990 | Dale et al. | | 5,192,282 A | 3/1993 | Draenert et al. |
| 4,893,974 A | 1/1990 | Fischer et al. | | 5,197,987 A | 3/1993 | Koch et al. |
| 4,895,148 A | 1/1990 | Bays et al. | | 5,203,784 A | 4/1993 | Ross et al. |
| 4,896,668 A | 1/1990 | Popoff et al. | | 5,203,787 A | 4/1993 | Noblitt et al. |
| 4,898,156 A | 2/1990 | Gatturna et al. | | 5,207,679 A | 5/1993 | Li |
| 4,899,743 A | 2/1990 | Nicholson et al. | | 5,209,753 A | 5/1993 | Biedermann et al. |
| 4,901,721 A | 2/1990 | Hakki | | 5,209,805 A | 5/1993 | Spraggins |
| 4,923,461 A | 5/1990 | Caspari et al. | | 5,211,647 A | 5/1993 | Schmieding |
| 4,927,421 A | 5/1990 | Goble et al. | | 5,211,650 A | 5/1993 | Noda |
| 4,946,377 A | 8/1990 | Kovach | | 5,214,987 A | 6/1993 | Fenton, Sr. |
| 4,946,468 A | 8/1990 | Li | | 5,219,359 A | 6/1993 | McQuilkin et al. |
| 4,950,270 A | 8/1990 | Bowman et al. | | 5,222,976 A | 6/1993 | Yoon |
| 4,950,285 A | 8/1990 | Wilk | | 5,224,946 A | 7/1993 | Hayhurst et al. |
| 4,960,381 A | 10/1990 | Niznick | | 5,230,699 A | 7/1993 | Grasinger |
| 4,961,741 A | 10/1990 | Hayhurst | | 5,232,436 A | 8/1993 | Janevski |
| 4,968,315 A | 11/1990 | Gatturna | | 5,234,435 A | 8/1993 | Seagrave, Jr. |
| 4,968,317 A | 11/1990 | Tormala et al. | | 5,235,238 A | 8/1993 | Nomura et al. |
| 4,969,886 A | 11/1990 | Cziffer et al. | | 5,236,445 A | 8/1993 | Hayhurst et al. |
| 4,976,736 A | 12/1990 | White et al. | | 5,236,461 A | 8/1993 | Forte |
| 4,978,350 A | 12/1990 | Wagenknecht et al. | | 5,242,447 A | 9/1993 | Borzone |
| 4,979,956 A | 12/1990 | Silvestrini | | 5,246,441 A | 9/1993 | Ross et al. |
| 4,983,176 A | 1/1991 | Cushman et al. | | 5,249,899 A | 10/1993 | Wilson |
| 4,988,351 A | 1/1991 | Paulos et al. | | 5,250,053 A | 10/1993 | Snyder |
| 4,994,074 A | 2/1991 | Bezwada et al. | | 5,258,015 A | 11/1993 | Li et al. |
| 4,997,433 A | 3/1991 | Goble et al. | | 5,258,016 A | 11/1993 | DiPoto et al. |
| 5,002,550 A | 3/1991 | Li | | 5,258,040 A | 11/1993 | Bruchman et al. |
| 5,002,562 A | 3/1991 | Oberlander | | 5,261,908 A | 11/1993 | Campbell, Jr. |
| 5,007,921 A | 4/1991 | Brown | | 5,268,001 A | 12/1993 | Nicholson et al. |
| 5,030,224 A | 7/1991 | Wright et al. | | 5,269,160 A | 12/1993 | Wood |
| 5,030,235 A | 7/1991 | Campbell, Jr. | | 5,269,783 A | 12/1993 | Sander |
| 5,037,422 A | 8/1991 | Hayhurst et al. | | 5,269,806 A | 12/1993 | Sardelis et al. |
| 5,041,129 A | 8/1991 | Hayhurst et al. | | 5,269,809 A | 12/1993 | Hayhurst et al. |
| 5,046,513 A | 9/1991 | Gatturna et al. | | 5,279,311 A | 1/1994 | Snyder |
| 5,047,030 A | 9/1991 | Draenert et al. | | 5,281,422 A | 1/1994 | Badylak et al. |
| 5,053,046 A | 10/1991 | Janese | | 5,282,809 A | 2/1994 | Kammerer et al. |
| 5,053,047 A | 10/1991 | Yoon | | 5,282,832 A | 2/1994 | Toso et al. |
| 5,059,201 A | 10/1991 | Asnis | | 5,282,867 A | 2/1994 | Mikhail |
| 5,059,206 A | 10/1991 | Winters | | 5,285,040 A | 2/1994 | Brandberg et al. |
| 5,061,277 A | 10/1991 | Carpentier et al. | | 5,290,217 A | 3/1994 | Campos |
| 5,062,344 A | 11/1991 | Gerker | | 5,306,301 A | 4/1994 | Graf et al. |
| 5,062,843 A | 11/1991 | Mahony, III | | 5,312,422 A | 5/1994 | Trott |
| 5,064,431 A | 11/1991 | Gilbertson et al. | | 5,312,438 A | 5/1994 | Johnson |
| 5,074,874 A | 12/1991 | Yoon et al. | | 5,318,566 A | 6/1994 | Miller |
| 5,078,731 A | 1/1992 | Hayhurst | | 5,318,575 A | 6/1994 | Chesterfield et al. |
| 5,078,843 A | 1/1992 | Pratt | | 5,318,577 A | 6/1994 | Li |
| 5,084,050 A | 1/1992 | Draenert | | 5,318,578 A | 6/1994 | Hasson |
| 5,084,058 A | 1/1992 | Li | | 5,320,115 A | 6/1994 | Kenna |
| 5,085,661 A | 2/1992 | Moss | | 5,320,626 A | 6/1994 | Schmieding |
| 5,087,263 A | 2/1992 | Li | | 5,320,633 A | 6/1994 | Allen et al. |
| 5,089,012 A | 2/1992 | Prou | | 5,324,308 A | 6/1994 | Pierce |
| 5,092,866 A | 3/1992 | Breard et al. | | 5,330,489 A | 7/1994 | Green et al. |
| 5,098,435 A | 3/1992 | Stednitz et al. | | 5,333,625 A | 8/1994 | Klein |
| 5,100,415 A | 3/1992 | Hayhurst | | 5,334,204 A | 8/1994 | Clewett et al. |
| 5,100,417 A | 3/1992 | Cerier et al. | | 5,336,229 A | 8/1994 | Noda |
| 5,116,337 A | 5/1992 | Johnson | | 5,336,231 A | 8/1994 | Adair |
| 5,116,373 A | 5/1992 | Jakob et al. | | 5,336,240 A | 8/1994 | Metzler et al. |
| 5,116,375 A | 5/1992 | Hofmann | | 5,339,870 A | 8/1994 | Green et al. |
| 5,123,913 A | 6/1992 | Wilk et al. | | 5,342,369 A | 8/1994 | Harryman, II |
| 5,123,914 A | 6/1992 | Cope | | 5,346,462 A | 9/1994 | Barber |
| 5,127,785 A | 7/1992 | Faucher et al. | | 5,354,298 A | 10/1994 | Lee et al. |
| 5,129,901 A | 7/1992 | Decoste | | 5,356,412 A | 10/1994 | Golds et al. |
| 5,129,902 A | 7/1992 | Goble et al. | | 5,356,413 A | 10/1994 | Martins et al. |
| 5,129,904 A | 7/1992 | Illi et al. | | 5,356,417 A | 10/1994 | Golds |
| 5,129,906 A | 7/1992 | Ross et al. | | 5,358,511 A | 10/1994 | Gatturna et al. |
| 5,139,498 A | 8/1992 | Astudillo Ley | | 5,360,431 A | 11/1994 | Puno et al. |
| 5,139,499 A | 8/1992 | Small et al. | | 5,362,294 A | 11/1994 | Seitzinger |
| 5,139,520 A | 8/1992 | Rosenberg | | 5,364,400 A | 11/1994 | Rego, Jr. et al. |
| 5,143,498 A | 9/1992 | Whitman | | 5,366,461 A | 11/1994 | Blasnik |
| 5,147,362 A | 9/1992 | Goble | | 5,368,599 A | 11/1994 | Hirsch et al. |
| 5,149,329 A | 9/1992 | Richardson | | 5,370,661 A | 12/1994 | Branch |
| 5,152,790 A | 10/1992 | Rosenberg et al. | | 5,370,662 A | 12/1994 | Stone et al. |

| | | | | | |
|---|---|---|---|---|---|
| 5,372,146 A | 12/1994 | Branch | 5,524,946 A | 6/1996 | Thompson |
| 5,372,604 A | 12/1994 | Trott | 5,527,321 A | 6/1996 | Hinchliffe |
| 5,372,821 A | 12/1994 | Badylak et al. | 5,527,342 A | 6/1996 | Pietrzak et al. |
| 5,374,268 A | 12/1994 | Sander | 5,527,343 A | 6/1996 | Bonutti |
| 5,379,492 A | 1/1995 | Glesser | 5,534,012 A | 7/1996 | Bonutti |
| 5,383,878 A | 1/1995 | Roger et al. | 5,536,270 A | 7/1996 | Songer et al. |
| 5,383,904 A | 1/1995 | Totakura et al. | 5,540,698 A | 7/1996 | Preissman |
| 5,391,171 A | 2/1995 | Schmieding | 5,540,703 A | 7/1996 | Barker, Jr. et al. |
| 5,391,176 A | 2/1995 | de la Torre | 5,540,718 A | 7/1996 | Bartlett |
| 5,391,182 A | 2/1995 | Chin | 5,545,168 A | 8/1996 | Burke |
| 5,393,302 A | 2/1995 | Clark et al. | 5,545,178 A | 8/1996 | Kensey et al. |
| RE34,871 E | 3/1995 | McGuire et al. | 5,545,180 A | 8/1996 | Le et al. |
| 5,397,356 A | 3/1995 | Goble et al. | 5,545,228 A | 8/1996 | Kambin |
| 5,403,328 A | 4/1995 | Shallman | 5,549,613 A | 8/1996 | Goble et al. |
| 5,403,329 A | 4/1995 | Hinchcliffe | 5,549,617 A | 8/1996 | Green et al. |
| 5,403,348 A | 4/1995 | Bonutti | 5,549,619 A | 8/1996 | Peters et al. |
| 5,405,359 A | 4/1995 | Pierce | 5,549,630 A | 8/1996 | Bonutti |
| 5,417,691 A | 5/1995 | Hayhurst | 5,549,631 A | 8/1996 | Bonutti |
| 5,417,698 A | 5/1995 | Green et al. | 5,562,683 A | 10/1996 | Chan |
| 5,417,712 A | 5/1995 | Whittaker et al. | 5,562,685 A | 10/1996 | Mollenauer et al. |
| 5,423,819 A | 6/1995 | Small et al. | 5,562,686 A | 10/1996 | Sauer et al. |
| 5,423,821 A | 6/1995 | Pasque | 5,569,269 A | 10/1996 | Hart et al. |
| 5,423,823 A | 6/1995 | Schmieding | 5,569,305 A | 10/1996 | Bonutti |
| 5,423,860 A | 6/1995 | Lizardi et al. | 5,571,090 A | 11/1996 | Sherts |
| 5,425,733 A | 6/1995 | Schmieding | 5,571,139 A | 11/1996 | Jenkins, Jr. |
| 5,425,766 A | 6/1995 | Bowald et al. | 5,572,655 A | 11/1996 | Tuljapurkar et al. |
| 5,433,751 A | 7/1995 | Christel et al. | 5,573,286 A | 11/1996 | Rogozinski |
| 5,437,680 A | 8/1995 | Yoon | 5,573,542 A | 11/1996 | Stevens |
| 5,437,685 A | 8/1995 | Blasnik | 5,573,548 A | 11/1996 | Nazre et al. |
| 5,439,684 A | 8/1995 | Prewett et al. | 5,577,299 A | 11/1996 | Thompson et al. |
| 5,441,508 A | 8/1995 | Gazielly et al. | 5,578,057 A | 11/1996 | Wenstrom, Jr. |
| 5,443,468 A | 8/1995 | Johnson | 5,584,695 A | 12/1996 | Lal Sachdeva et al. |
| 5,443,482 A | 8/1995 | Stone et al. | 5,584,835 A | 12/1996 | Greenfield |
| 5,443,483 A | 8/1995 | Kirsch et al. | 5,584,836 A | 12/1996 | Ballintyn et al. |
| 5,443,509 A | 8/1995 | Boucher et al. | 5,584,862 A | 12/1996 | Bonutti |
| 5,445,833 A | 8/1995 | Badylak et al. | 5,586,986 A | 12/1996 | Hinchliffe |
| 5,447,512 A | 9/1995 | Wilson et al. | 5,588,575 A | 12/1996 | Davignon |
| 5,449,361 A | 9/1995 | Preissman | 5,591,180 A | 1/1997 | Hinchliffe |
| 5,451,203 A | 9/1995 | Lamb | 5,591,181 A | 1/1997 | Stone et al. |
| 5,454,811 A | 10/1995 | Huebner | 5,591,207 A | 1/1997 | Coleman |
| 5,454,821 A | 10/1995 | Harm et al. | 5,593,407 A | 1/1997 | Reis et al. |
| 5,456,685 A | 10/1995 | Huebner | 5,593,425 A | 1/1997 | Bonutti et al. |
| 5,456,722 A | 10/1995 | McLeod et al. | 5,601,557 A | 2/1997 | Hayhurst |
| 5,458,601 A | 10/1995 | Young, Jr. et al. | 5,601,559 A | 2/1997 | Melker et al. |
| 5,458,604 A | 10/1995 | Schmieding | 5,601,571 A | 2/1997 | Moss |
| 5,462,542 A | 10/1995 | Alesi, Jr. | 5,603,716 A | 2/1997 | Morgan et al. |
| 5,462,560 A | 10/1995 | Stevens | 5,607,429 A | 3/1997 | Hayano et al. |
| 5,464,426 A | 11/1995 | Bonutti | 5,618,290 A | 4/1997 | Toy et al. |
| 5,464,427 A | 11/1995 | Curtis et al. | 5,626,611 A | 5/1997 | Liu et al. |
| 5,464,440 A | 11/1995 | Johansson et al. | 5,626,614 A | 5/1997 | Hart |
| 5,466,237 A | 11/1995 | Byrd, III et al. | 5,628,756 A | 5/1997 | Barker, Jr. et al. |
| 5,467,786 A | 11/1995 | Allen et al. | 5,628,766 A | 5/1997 | Johnson |
| 5,470,334 A | 11/1995 | Ross et al. | 5,630,824 A | 5/1997 | Hart |
| 5,470,337 A | 11/1995 | Moss | 5,632,748 A | 5/1997 | Beck, Jr. et al. |
| 5,470,338 A | 11/1995 | Whitfield et al. | 5,641,256 A | 6/1997 | Gundy |
| 5,472,452 A | 12/1995 | Trott | 5,643,266 A | 7/1997 | Li |
| 5,474,565 A | 12/1995 | Trott | 5,643,269 A | 7/1997 | Harle et al. |
| 5,474,568 A | 12/1995 | Scott | 5,643,295 A | 7/1997 | Yoon |
| 5,474,572 A | 12/1995 | Hayhurst | 5,643,319 A | 7/1997 | Green et al. |
| 5,478,344 A | 12/1995 | Stone et al. | 5,643,320 A | 7/1997 | Lower et al. |
| 5,478,345 A | 12/1995 | Stone et al. | 5,643,321 A | 7/1997 | McDevitt |
| 5,480,403 A | 1/1996 | Lee et al. | 5,645,546 A | 7/1997 | Fard |
| 5,480,406 A | 1/1996 | Nolan et al. | 5,645,547 A | 7/1997 | Coleman |
| 5,484,442 A | 1/1996 | Melker et al. | 5,645,568 A | 7/1997 | Chervitz et al. |
| 5,486,197 A | 1/1996 | Le et al. | 5,645,588 A | 7/1997 | Graf et al. |
| 5,490,750 A | 2/1996 | Gundy | 5,647,874 A | 7/1997 | Hayhurst |
| 5,496,331 A | 3/1996 | Xu et al. | 5,649,959 A | 7/1997 | Hannam et al. |
| 5,496,348 A | 3/1996 | Bonutti | 5,649,963 A | 7/1997 | McDevitt |
| 5,500,000 A | 3/1996 | Feagin et al. | 5,658,289 A | 8/1997 | Boucher et al. |
| 5,505,736 A | 4/1996 | Reimels et al. | 5,658,299 A | 8/1997 | Hart |
| 5,507,754 A | 4/1996 | Green et al. | 5,658,313 A | 8/1997 | Thal |
| 5,520,691 A | 5/1996 | Branch | 5,662,658 A | 9/1997 | Wenstrom, Jr. |
| 5,520,700 A | 5/1996 | Beyar et al. | 5,662,663 A | 9/1997 | Shallman |
| 5,520,702 A | 5/1996 | Sauer et al. | 5,665,112 A | 9/1997 | Thal |
| 5,522,817 A | 6/1996 | Sander et al. | 5,667,513 A | 9/1997 | Torrie et al. |
| 5,522,820 A | 6/1996 | Caspari et al. | 5,671,695 A | 9/1997 | Schroeder |
| 5,522,844 A | 6/1996 | Johnson | 5,674,224 A | 10/1997 | Howell et al. |
| 5,522,845 A | 6/1996 | Wenstrom, Jr. | 5,679,723 A | 10/1997 | Cooper et al. |
| 5,522,846 A | 6/1996 | Bonutti | 5,681,334 A | 10/1997 | Evans et al. |

| | | | | | | |
|---|---|---|---|---|---|---|
| 5,681,352 A | 10/1997 | Clancy, III et al. | | 5,860,973 A | 1/1999 | Michelson |
| 5,683,419 A | 11/1997 | Thal | | 5,868,740 A | 2/1999 | LeVeen et al. |
| 5,688,285 A | 11/1997 | Yamada et al. | | 5,868,748 A | 2/1999 | Burke |
| 5,690,676 A | 11/1997 | DiPoto et al. | | 5,868,789 A | 2/1999 | Huebner |
| 5,690,678 A | 11/1997 | Johnson | | 5,871,484 A | 2/1999 | Spievack et al. |
| 5,693,046 A | 12/1997 | Songer et al. | | 5,871,486 A | 2/1999 | Huebner et al. |
| 5,695,497 A | 12/1997 | Stahelin et al. | | 5,871,490 A | 2/1999 | Schulze et al. |
| 5,697,929 A | 12/1997 | Mellinger | | 5,885,294 A | 3/1999 | Pedlick et al. |
| 5,699,657 A | 12/1997 | Paulson | | 5,891,168 A | 4/1999 | Thal |
| 5,702,397 A | 12/1997 | Goble et al. | | 5,893,592 A | 4/1999 | Schulze et al. |
| 5,702,422 A | 12/1997 | Stone | | 5,895,395 A | 4/1999 | Yeung |
| 5,702,462 A | 12/1997 | Oberlander | | 5,897,564 A | 4/1999 | Schulze et al. |
| 5,707,373 A | 1/1998 | Sevrain et al. | | 5,897,574 A | 4/1999 | Bonutti |
| 5,711,969 A | 1/1998 | Patel et al. | | 5,899,902 A | 5/1999 | Brown et al. |
| 5,713,005 A | 1/1998 | Proebsting | | 5,899,938 A | 5/1999 | Sklar et al. |
| 5,713,904 A | 2/1998 | Errico et al. | | 5,908,421 A | 6/1999 | Beger et al. |
| 5,713,905 A | 2/1998 | Goble et al. | | 5,908,436 A | 6/1999 | Cuschieri et al. |
| 5,713,921 A | 2/1998 | Bonutti | | 5,910,148 A | 6/1999 | Reimels et al. |
| 5,716,359 A | 2/1998 | Ojima et al. | | 5,911,721 A | 6/1999 | Nicholson et al. |
| 5,716,397 A | 2/1998 | Myers | | 5,918,604 A | 7/1999 | Whelan |
| 5,718,717 A | 2/1998 | Bonutti | | 5,921,986 A | 7/1999 | Bonutti |
| 5,720,747 A | 2/1998 | Burke | | 5,925,008 A | 7/1999 | Douglas |
| 5,720,765 A | 2/1998 | Thal | | 5,928,231 A | 7/1999 | Klein et al. |
| 5,720,766 A | 2/1998 | Zang et al. | | 5,928,267 A | 7/1999 | Bonutti et al. |
| 5,722,976 A | 3/1998 | Brown | | RE36,289 E | 8/1999 | Le et al. |
| 5,725,549 A | 3/1998 | Lam | | 5,931,838 A | 8/1999 | Vito |
| 5,725,556 A | 3/1998 | Moser et al. | | 5,931,844 A | 8/1999 | Thompson et al. |
| 5,725,581 A | 3/1998 | Br.ang.nemark | | 5,931,869 A | 8/1999 | Boucher et al. |
| 5,725,582 A | 3/1998 | Bevan et al. | | 5,935,119 A | 8/1999 | Guy et al. |
| 5,726,722 A | 3/1998 | Uehara et al. | | 5,935,133 A | 8/1999 | Wagner et al. |
| 5,728,107 A | 3/1998 | Zlock et al. | | 5,935,149 A | 8/1999 | Ek |
| 5,728,109 A | 3/1998 | Schulze et al. | | 5,938,668 A | 8/1999 | Scirica et al. |
| 5,728,136 A | 3/1998 | Thal | | 5,941,439 A * | 8/1999 | Kammerer et al. ............ 227/67 |
| 5,733,293 A | 3/1998 | Scirica et al. | | 5,941,900 A | 8/1999 | Bonutti |
| 5,733,306 A | 3/1998 | Bonutti | | 5,944,739 A | 8/1999 | Zlock et al. |
| 5,733,307 A | 3/1998 | Dinsdale | | 5,946,783 A | 9/1999 | Plociennik et al. |
| 5,735,875 A | 4/1998 | Bonutti et al. | | 5,947,915 A | 9/1999 | Thibodo, Jr. |
| 5,741,259 A | 4/1998 | Chan | | 5,947,982 A | 9/1999 | Duran |
| 5,741,260 A | 4/1998 | Songer et al. | | 5,947,999 A | 9/1999 | Groiso |
| 5,741,281 A | 4/1998 | Martin et al. | | 5,948,002 A | 9/1999 | Bonutti |
| 5,743,912 A | 4/1998 | Lahille et al. | | 5,951,559 A | 9/1999 | Burkhart |
| 5,746,751 A | 5/1998 | Sherts | | 5,951,560 A | 9/1999 | Simon et al. |
| 5,746,752 A | 5/1998 | Burkhart | | 5,954,747 A | 9/1999 | Clark |
| 5,746,754 A | 5/1998 | Chan | | 5,957,953 A | 9/1999 | DiPoto et al. |
| 5,749,898 A | 5/1998 | Schulze et al. | | 5,961,521 A | 10/1999 | Roger et al. |
| 5,755,729 A | 5/1998 | de la Torre et al. | | 5,961,524 A | 10/1999 | Crombie |
| 5,755,791 A | 5/1998 | Whitson et al. | | 5,964,764 A | 10/1999 | West, Jr. et al. |
| 5,766,176 A | 6/1998 | Duncan | | 5,964,767 A | 10/1999 | Tapia et al. |
| 5,766,218 A | 6/1998 | Arnott | | 5,964,769 A | 10/1999 | Wagner et al. |
| 5,766,250 A | 6/1998 | Chervitz et al. | | 5,964,783 A | 10/1999 | Grafton et al. |
| 5,769,894 A | 6/1998 | Ferragamo | | 5,968,045 A | 10/1999 | Frazier |
| 5,769,899 A | 6/1998 | Schwartz et al. | | 5,968,047 A | 10/1999 | Reed |
| 5,772,673 A | 6/1998 | Cuny et al. | | 5,968,077 A | 10/1999 | Wojciechowicz et al. |
| 5,776,196 A | 7/1998 | Matsuzaki et al. | | 5,972,006 A | 10/1999 | Sciaino, Jr. |
| 5,782,845 A | 7/1998 | Shewchuk | | 5,976,125 A | 11/1999 | Graham |
| 5,782,862 A | 7/1998 | Bonutti | | 5,976,127 A | 11/1999 | Lax |
| 5,782,864 A | 7/1998 | Lizardi | | 5,980,524 A | 11/1999 | Justin et al. |
| 5,782,866 A | 7/1998 | Wenstrom, Jr. | | 5,980,539 A | 11/1999 | Kontos |
| 5,785,714 A | 7/1998 | Morgan et al. | | 5,980,558 A | 11/1999 | Wiley |
| 5,792,142 A | 8/1998 | Galitzer | | 5,980,559 A | 11/1999 | Bonutti |
| 5,792,149 A | 8/1998 | Sherts et al. | | 5,989,252 A | 11/1999 | Fumex |
| 5,796,127 A | 8/1998 | Hayafuji et al. | | 5,989,256 A | 11/1999 | Kuslich et al. |
| 5,797,915 A | 8/1998 | Pierson, III et al. | | 5,989,282 A | 11/1999 | Bonutti |
| 5,797,928 A | 8/1998 | Kogasaka | | 5,993,452 A | 11/1999 | Vandewalle |
| 5,800,407 A | 9/1998 | Eldor et al. | | 5,993,476 A | 11/1999 | Groiso |
| 5,810,824 A | 9/1998 | Chan | | 5,997,542 A | 12/1999 | Burke |
| 5,810,848 A * | 9/1998 | Hayhurst ...................... 606/144 | | 5,997,552 A | 12/1999 | Person et al. |
| 5,814,069 A | 9/1998 | Schulze et al. | | 5,997,575 A | 12/1999 | Whitson et al. |
| 5,814,070 A | 9/1998 | Borzone et al. | | 6,001,100 A | 12/1999 | Sherman et al. |
| 5,814,072 A | 9/1998 | Bonutti | | 6,007,538 A | 12/1999 | Levin |
| 5,814,073 A | 9/1998 | Bonutti | | 6,007,567 A | 12/1999 | Bonutti |
| 5,823,980 A | 10/1998 | Kopfer | | 6,010,525 A | 1/2000 | Bonutti et al. |
| 5,824,011 A | 10/1998 | Stone et al. | | 6,016,727 A | 1/2000 | Morgan |
| 5,830,234 A | 11/1998 | Wojciechowicz et al. | | 6,022,352 A | 2/2000 | Vandewalle |
| 5,843,084 A | 12/1998 | Hart et al. | | 6,022,373 A | 2/2000 | Li |
| 5,845,645 A | 12/1998 | Bonutti | | 6,024,758 A | 2/2000 | Thal |
| 5,846,254 A | 12/1998 | Schulze et al. | | 6,027,523 A | 2/2000 | Schmieding |
| 5,848,983 A | 12/1998 | Basaj et al. | | 6,030,410 A | 2/2000 | Zurbrugg |
| 5,849,012 A | 12/1998 | Abboudi | | 6,033,429 A | 3/2000 | Magovern |

| | | | |
|---|---|---|---|
| 6,033,430 A | 3/2000 | Bonutti | |
| 6,039,753 A * | 3/2000 | Meislin .................. 606/213 | |
| 6,041,485 A | 3/2000 | Pedlick et al. | |
| 6,042,601 A | 3/2000 | Smith | |
| 6,045,551 A | 4/2000 | Bonutti | |
| 6,045,571 A | 4/2000 | Hill et al. | |
| 6,045,572 A | 4/2000 | Johnson et al. | |
| 6,045,573 A | 4/2000 | Wenstrom, Jr. et al. | |
| 6,045,574 A | 4/2000 | Thal | |
| 6,047,826 A | 4/2000 | Kalinski et al. | |
| 6,048,343 A | 4/2000 | Mathis et al. | |
| 6,051,006 A | 4/2000 | Shluzas et al. | |
| 6,051,007 A | 4/2000 | Hogendijk et al. | |
| 6,053,916 A | 4/2000 | Moore | |
| 6,053,921 A | 4/2000 | Wagner et al. | |
| 6,056,752 A | 5/2000 | Roger et al. | |
| 6,056,772 A | 5/2000 | Bonutti | |
| 6,056,773 A | 5/2000 | Bonutti | |
| 6,059,817 A | 5/2000 | Bonutti et al. | |
| 6,059,818 A | 5/2000 | Johnson et al. | |
| 6,062,344 A | 5/2000 | Okabe et al. | |
| 6,068,648 A | 5/2000 | Cole et al. | |
| 6,071,305 A | 6/2000 | Brown et al. | |
| 6,074,403 A | 6/2000 | Nord | |
| 6,077,277 A | 6/2000 | Mollenauer et al. | |
| 6,077,292 A | 6/2000 | Bonutti | |
| 6,080,185 A | 6/2000 | Johnson et al. | |
| 6,086,591 A | 7/2000 | Bojarski | |
| 6,086,592 A | 7/2000 | Rosenberg et al. | |
| 6,086,608 A | 7/2000 | Ek et al. | |
| 6,093,200 A | 7/2000 | Liu et al. | |
| 6,096,060 A | 8/2000 | Fitts et al. | |
| 6,099,527 A | 8/2000 | Hochschuler et al. | |
| 6,099,530 A | 8/2000 | Simonian et al. | |
| 6,099,568 A | 8/2000 | Simonian et al. | |
| 6,106,545 A | 8/2000 | Egan | |
| 6,110,128 A | 8/2000 | Andelin et al. | |
| 6,117,160 A | 9/2000 | Bonutti | |
| 6,117,162 A | 9/2000 | Schmieding et al. | |
| 6,123,710 A | 9/2000 | Pinczewski et al. | |
| 6,132,433 A | 10/2000 | Whelan | |
| 6,132,437 A | 10/2000 | Omurtag et al. | |
| 6,139,565 A | 10/2000 | Stone et al. | |
| RE36,974 E | 11/2000 | Bonutti | |
| 6,143,017 A | 11/2000 | Thal | |
| 6,146,406 A | 11/2000 | Shluzas et al. | |
| 6,146,408 A | 11/2000 | Bartlett | |
| 6,149,653 A | 11/2000 | Deslauriers | |
| 6,149,669 A | 11/2000 | Li | |
| 6,152,928 A | 11/2000 | Wenstrom, Jr. | |
| 6,152,934 A | 11/2000 | Harper et al. | |
| 6,152,936 A | 11/2000 | Christy et al. | |
| 6,152,949 A | 11/2000 | Bonutti | |
| 6,156,039 A | 12/2000 | Thal | |
| 6,156,056 A | 12/2000 | Kearns et al. | |
| 6,159,234 A | 12/2000 | Bonutti et al. | |
| 6,165,203 A | 12/2000 | Krebs | |
| 6,168,598 B1 | 1/2001 | Martello | |
| 6,168,628 B1 | 1/2001 | Huebner | |
| 6,179,840 B1 | 1/2001 | Bowman | |
| 6,183,461 B1 | 2/2001 | Matsuura et al. | |
| 6,187,025 B1 | 2/2001 | Machek | |
| 6,190,401 B1 | 2/2001 | Green et al. | |
| 6,190,411 B1 | 2/2001 | Lo et al. | |
| 6,193,754 B1 | 2/2001 | Seedhom et al. | |
| 6,200,318 B1 | 3/2001 | Har-Shai et al. | |
| 6,200,329 B1 | 3/2001 | Fung et al. | |
| 6,200,330 B1 | 3/2001 | Benderev et al. | |
| 6,203,556 B1 | 3/2001 | Evans et al. | |
| 6,203,565 B1 | 3/2001 | Bonutti et al. | |
| 6,203,572 B1 | 3/2001 | Johnson et al. | |
| 6,206,883 B1 | 3/2001 | Tunc | |
| 6,210,376 B1 | 4/2001 | Grayson | |
| 6,214,012 B1 | 4/2001 | Karpman et al. | |
| 6,217,580 B1 | 4/2001 | Levin | |
| 6,221,107 B1 | 4/2001 | Steiner et al. | |
| 6,228,096 B1 | 5/2001 | Marchand | |
| 6,231,592 B1 | 5/2001 | Bonutti et al. | |
| 6,235,057 B1 | 5/2001 | Roger et al. | |
| 6,238,395 B1 | 5/2001 | Bonutti | |
| 6,241,734 B1 | 6/2001 | Scribner et al. | |
| 6,241,747 B1 | 6/2001 | Ruff | |
| 6,241,771 B1 | 6/2001 | Gresser et al. | |
| 6,245,081 B1 | 6/2001 | Bowman et al. | |
| 6,258,091 B1 | 7/2001 | Sevrain et al. | |
| 6,267,766 B1 | 7/2001 | Burkhart | |
| 6,269,716 B1 | 8/2001 | Amis | |
| 6,270,518 B1 | 8/2001 | Pedlick et al. | |
| 6,273,890 B1 | 8/2001 | Frazier | |
| 6,283,973 B1 | 9/2001 | Hubbard et al. | |
| 6,283,996 B1 | 9/2001 | Chervitz et al. | |
| 6,287,307 B1 | 9/2001 | Abboudi | |
| 6,287,325 B1 | 9/2001 | Bonutti | |
| 6,293,961 B2 | 9/2001 | Schwartz et al. | |
| 6,296,659 B1 | 10/2001 | Foerster | |
| 6,299,615 B1 | 10/2001 | Huebner | |
| 6,302,888 B1 | 10/2001 | Mellinger et al. | |
| 6,302,899 B1 | 10/2001 | Johnson et al. | |
| 6,306,156 B1 | 10/2001 | Clark | |
| 6,306,159 B1 | 10/2001 | Schwartz et al. | |
| 6,309,405 B1 | 10/2001 | Bonutti | |
| 6,312,448 B1 | 11/2001 | Bonutti | |
| 6,315,788 B1 | 11/2001 | Roby | |
| 6,319,271 B1 | 11/2001 | Schwartz et al. | |
| 6,328,758 B1 | 12/2001 | Tornier et al. | |
| 6,342,060 B1 | 1/2002 | Adams | |
| 6,343,531 B2 | 2/2002 | Amis | |
| 6,358,270 B1 | 3/2002 | Lemer | |
| 6,364,897 B1 | 4/2002 | Bonutti | |
| 6,368,322 B1 | 4/2002 | Luks et al. | |
| 6,368,326 B1 | 4/2002 | Dakin et al. | |
| 6,368,343 B1 | 4/2002 | Bonutti et al. | |
| 6,371,124 B1 | 4/2002 | Whelan | |
| 6,379,361 B1 | 4/2002 | Beck, Jr. et al. | |
| 6,383,190 B1 | 5/2002 | Preissman | |
| 6,383,199 B2 | 5/2002 | Carter et al. | |
| 6,387,113 B1 | 5/2002 | Hawkins et al. | |
| 6,387,129 B2 | 5/2002 | Rieser et al. | |
| 6,391,030 B1 | 5/2002 | Wagner et al. | |
| 6,398,785 B2 | 6/2002 | Carchidi et al. | |
| 6,406,479 B1 | 6/2002 | Justin et al. | |
| 6,409,743 B1 | 6/2002 | Fenton, Jr. | |
| 6,413,260 B1 | 7/2002 | Berrevoets et al. | |
| 6,423,088 B1 | 7/2002 | Fenton, Jr. | |
| 6,428,562 B2 | 8/2002 | Bonutti | |
| 6,432,123 B2 | 8/2002 | Schwartz et al. | |
| 6,436,123 B2 | 8/2002 | Magovern | |
| 6,436,124 B1 | 8/2002 | Anderson et al. | |
| 6,440,134 B1 | 8/2002 | Zaccherotti et al. | |
| 6,440,136 B1 | 8/2002 | Gambale et al. | |
| 6,447,516 B1 | 9/2002 | Bonutti | |
| 6,451,030 B2 | 9/2002 | Li et al. | |
| 6,454,768 B1 | 9/2002 | Jackson | |
| 6,458,134 B1 | 10/2002 | Songer et al. | |
| 6,461,373 B2 | 10/2002 | Wyman et al. | |
| 6,464,713 B2 | 10/2002 | Bonutti | |
| 6,468,293 B2 | 10/2002 | Bonutti et al. | |
| 6,471,707 B1 | 10/2002 | Miller et al. | |
| 6,475,230 B1 | 11/2002 | Bonutti et al. | |
| 6,482,210 B1 | 11/2002 | Skiba et al. | |
| 6,485,504 B1 | 11/2002 | Johnson et al. | |
| 6,497,901 B1 | 12/2002 | Royer | |
| 6,500,184 B1 | 12/2002 | Chan et al. | |
| 6,500,195 B2 | 12/2002 | Bonutti | |
| RE37,963 E | 1/2003 | Thal | |
| 6,503,267 B2 | 1/2003 | Bonutti et al. | |
| 6,506,190 B1 | 1/2003 | Walshe | |
| 6,508,820 B2 | 1/2003 | Bales | |
| 6,508,821 B1 | 1/2003 | Schwartz et al. | |
| 6,508,830 B2 | 1/2003 | Steiner | |
| 6,511,498 B1 | 1/2003 | Fumex et al. | |
| 6,511,499 B2 | 1/2003 | Schmieding et al. | |
| 6,517,542 B1 | 2/2003 | Papay et al. | |
| 6,517,552 B1 | 2/2003 | Nord et al. | |
| 6,517,578 B2 | 2/2003 | Hein et al. | |
| 6,517,579 B1 | 2/2003 | Paulos et al. | |
| 6,520,964 B2 | 2/2003 | Tallarida et al. | |
| 6,520,980 B1 | 2/2003 | Foerster | |

| | | |
|---|---|---|
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B1 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 * | 8/2004 | Bailly et al. ............. 227/176.1 |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,001,429 B2 | 2/2006 | Ferguson |
| 7,004,959 B2 | 2/2006 | Bonutti |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,105,010 B2 | 9/2006 | Hart et al. |
| 7,112,221 B2 | 9/2006 | Harris |
| 7,118,583 B2 | 10/2006 | O'Quinn et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |
| 7,201,722 B2 | 4/2007 | Krueger |
| 7,255,675 B2 | 8/2007 | Gertner et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |

| | | |
|---|---|---|
| 7,303,577 B1 | 12/2007 | Dean |
| 7,306,417 B2 | 12/2007 | Dorstewitz |
| 7,326,222 B2 | 2/2008 | Dreyfuss et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,513,910 B2 | 4/2009 | Buskirk et al. |
| 7,578,825 B2 | 8/2009 | Huebner |
| 7,585,311 B2 | 9/2009 | Green et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 7,981,140 B2 | 7/2011 | Burkhart |
| 8,062,334 B2 | 11/2011 | Green et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller, III |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |

| Publication No. | Date | Inventor |
|---|---|---|
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 * | 8/2006 | Nelson et al. .................. 606/139 |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0235407 A1 | 10/2006 | Wang et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |

| | | | | | | |
|---|---|---|---|---|---|---|
| 2009/0054928 A1 | 2/2009 | Denham et al. | DE | 3136083 | | 3/1983 |
| 2009/0062854 A1 | 3/2009 | Kaiser et al. | DE | 233303 | | 2/1986 |
| 2009/0082790 A1 | 3/2009 | Shad et al. | DE | 4127550 | | 2/1993 |
| 2009/0082805 A1 | 3/2009 | Kaiser et al. | DE | 4302397 | | 7/1993 |
| 2009/0099598 A1 | 4/2009 | McDevitt et al. | DE | 29621340 | | 5/1998 |
| 2009/0105754 A1 | 4/2009 | Sethi | DE | 19841252 | | 3/2000 |
| 2009/0118774 A1 | 5/2009 | Miller, III | EP | 0108912 | | 5/1984 |
| 2009/0118775 A1 | 5/2009 | Burke | EP | 0129442 | | 12/1984 |
| 2009/0125073 A1 | 5/2009 | Rehm | EP | 0172130 | | 2/1986 |
| 2009/0138002 A1 | 5/2009 | Fenton | EP | 0241240 | | 10/1987 |
| 2009/0138054 A1 | 5/2009 | Teague et al. | EP | 0241792 | | 10/1987 |
| 2009/0156997 A1 | 6/2009 | Trenhaile | EP | 0260970 | | 3/1988 |
| 2009/0163949 A1 | 6/2009 | Rolnick et al. | EP | 0270704 | | 6/1988 |
| 2009/0177233 A1 | 7/2009 | Malek | EP | 0282789 | | 9/1988 |
| 2009/0192468 A1 | 7/2009 | Stone | EP | 0315371 | | 5/1989 |
| 2009/0198277 A1 | 8/2009 | Gordon et al. | EP | 0317406 | | 5/1989 |
| 2009/0204146 A1 | 8/2009 | Kaiser et al. | EP | 0340159 | | 11/1989 |
| 2009/0228042 A1 | 9/2009 | Koogle, Jr. et al. | EP | 0346183 | | 12/1989 |
| 2009/0234357 A1 | 9/2009 | Morales et al. | EP | 0349173 | | 1/1990 |
| 2009/0234358 A1 | 9/2009 | Morales et al. | EP | 0374088 | | 6/1990 |
| 2009/0240251 A1 | 9/2009 | Gabele | EP | 0409364 | | 1/1991 |
| 2009/0248091 A1 | 10/2009 | Teague et al. | EP | 0415915 | | 3/1991 |
| 2009/0265014 A1 | 10/2009 | May et al. | EP | 0440991 | | 8/1991 |
| 2009/0306711 A1 | 12/2009 | Stone et al. | EP | 0441065 | | 8/1991 |
| 2009/0312776 A1 | 12/2009 | Kaiser et al. | EP | 0451932 | | 10/1991 |
| 2009/0318960 A1 | 12/2009 | Burkhart | EP | 0464480 | | 1/1992 |
| 2009/0318961 A1 | 12/2009 | Stone et al. | EP | 0497079 | | 8/1992 |
| 2010/0042114 A1 | 2/2010 | Schaffhausen | EP | 0502509 | | 9/1992 |
| 2010/0087857 A1 | 4/2010 | Stone et al. | EP | 0502698 | | 9/1992 |
| 2010/0145384 A1 | 6/2010 | Stone et al. | EP | 520177 | | 12/1992 |
| 2010/0191342 A1 | 7/2010 | Byrd et al. | EP | 0546726 | | 6/1993 |
| 2010/0211075 A1 | 8/2010 | Stone | EP | 0574707 | | 12/1993 |
| 2010/0256677 A1 | 10/2010 | Albertorio et al. | EP | 0582514 | | 2/1994 |
| 2010/0268273 A1 | 10/2010 | Albertorio et al. | EP | 0591991 | | 4/1994 |
| 2010/0268275 A1 | 10/2010 | Stone et al. | EP | 0598219 | | 5/1994 |
| 2010/0270306 A1 | 10/2010 | Shiffer | EP | 0611551 | A1 | 8/1994 |
| 2010/0292792 A1 | 11/2010 | Stone et al. | EP | 0627203 | | 12/1994 |
| 2010/0305698 A1 | 12/2010 | Metzger et al. | EP | 0651979 | | 5/1995 |
| 2010/0305709 A1 | 12/2010 | Metzger et al. | EP | 0669110 | | 8/1995 |
| 2010/0312341 A1 | 12/2010 | Kaiser et al. | EP | 0686373 | | 12/1995 |
| 2011/0009885 A1 | 1/2011 | Graf et al. | EP | 0702933 | | 3/1996 |
| 2011/0087284 A1 | 4/2011 | Stone et al. | EP | 0775473 | | 5/1997 |
| 2011/0098727 A1 | 4/2011 | Kaiser et al. | EP | 0913123 | | 5/1999 |
| 2011/0106153 A1 | 5/2011 | Stone et al. | EP | 0913131 | | 5/1999 |
| 2011/0160767 A1 | 6/2011 | Stone et al. | EP | 99121106 | | 10/1999 |
| 2011/0160768 A1 | 6/2011 | Stone et al. | EP | 991210527 | | 10/1999 |
| 2011/0208239 A1 | 8/2011 | Stone et al. | EP | 0995409 | | 4/2000 |
| 2011/0208240 A1 | 8/2011 | Stone et al. | EP | 1013229 | | 6/2000 |
| 2011/0213416 A1 | 9/2011 | Kaiser | EP | 1093773 | | 4/2001 |
| 2011/0218625 A1 | 9/2011 | Berelsman et al. | EP | 1093774 | | 4/2001 |
| 2011/0224799 A1 | 9/2011 | Stone | EP | 1555945 | | 7/2005 |
| 2011/0264141 A1 | 10/2011 | Denham et al. | FR | 2622790 | | 5/1989 |
| 2011/0270278 A1 | 11/2011 | Overes et al. | FR | 2655840 | | 6/1991 |
| 2011/0270306 A1 | 11/2011 | Denham et al. | FR | 2682867 | | 4/1993 |
| 2012/0041485 A1 | 2/2012 | Kaiser et al. | FR | 2687911 | | 9/1993 |
| 2012/0041486 A1 | 2/2012 | Stone et al. | FR | 2688689 | | 9/1993 |
| 2012/0046693 A1 | 2/2012 | Denham et al. | FR | 2704140 | | 10/1994 |
| 2012/0053630 A1 | 3/2012 | Denham et al. | FR | 2717070 | | 9/1995 |
| 2012/0059417 A1 | 3/2012 | Norton et al. | FR | 2723528 | | 2/1996 |
| 2012/0059418 A1 | 3/2012 | Denham et al. | FR | 2744010 | | 8/1997 |
| 2012/0197271 A1 | 8/2012 | Astorino et al. | FR | 2745999 | | 9/1997 |
| FOREIGN PATENT DOCUMENTS | | | FR | 2770764 | | 5/1999 |
| | | | GB | 401677 | | 11/1933 |
| AU | 440266 | 10/1967 | GB | 1413477 | | 11/1975 |
| AU | 2223767 | 11/1968 | GB | 1485681 | | 9/1977 |
| AU | 5850469 | 1/1971 | GB | 2083751 | | 3/1982 |
| AU | 5963869 | 2/1971 | GB | 2118474 | | 11/1983 |
| AU | 1505470 | 11/1971 | GB | 2227175 | | 7/1990 |
| AU | 3615171 | 5/1973 | GB | 2253147 | | 9/1992 |
| AU | 5028569 | 9/1973 | GB | 2312376 | | 10/1997 |
| AU | 7110887 | 10/1987 | GB | 2403416 | A | 1/2005 |
| AU | 639410 | 11/1989 | JP | 5362911 | | 5/1978 |
| AU | 651929 | 8/1994 | JP | 5362912 | | 5/1978 |
| DE | 2529669 | 3/1976 | JP | 5374942 | | 6/1978 |
| DE | 2747312 | 4/1979 | JP | 5378230 | | 6/1978 |
| DE | 2818254 | 10/1979 | JP | 62159647 | | 7/1987 |
| DE | 2919009 | 11/1979 | JP | 62295657 | | 12/1987 |
| DE | 3027138 | 12/1981 | JP | 5269160 | | 10/1993 |
| DE | 3225620 | 2/1983 | JP | 5300917 | | 11/1993 |

| | | |
|---|---|---|
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2008002550 A2 | 1/2008 |
| WO | WO-2009012021 A1 | 1/2009 |

OTHER PUBLICATIONS

"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"Make your next tendon repair an open-and-shut case. The Teno Fix® Tendon Repair System", Teno Fix® brochure, 2003 (2 pages) Ortheon® Medical.

"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Lawhom, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jun. 9, 2011 for PCT/US2001/026349 claiming benefit of U.S. Appl. No. 12/938,902, filed Nov. 3, 2010; and U.S. Appl. No. 12/719,337, filed Mar. 8, 2010.
"Arthroscopic Meniscal Repair using the Meniscal Cinch™", Surgical Technique brochure. (2008) Arthrex® 6 sheets.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
Invitation to Pay Additional Fees mailed Jul. 19, 2012, for PCT/US2012/037703 claiming benefit of U.S. Appl. No. 13/109,667, filed May 7, 2011.
International Preliminary Report on Patentability and Written Opinion mailed Sep. 20, 2012 for PCT/US2011/026349 claiming benefit of U.S. Appl. No. 12/938,902, filed Nov. 3, 2010.
US 6,238,418, 05/2001, Schwartz et al. (withdrawn)

* cited by examiner

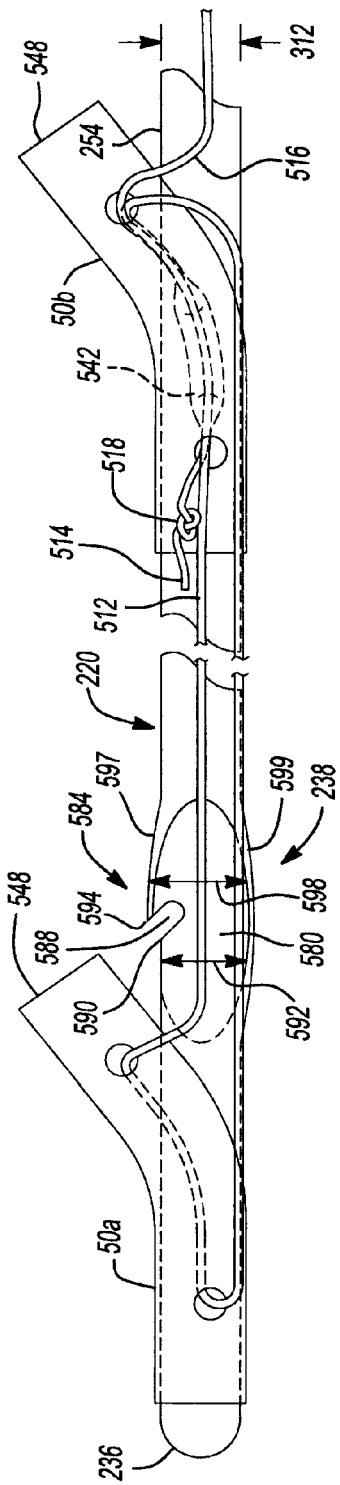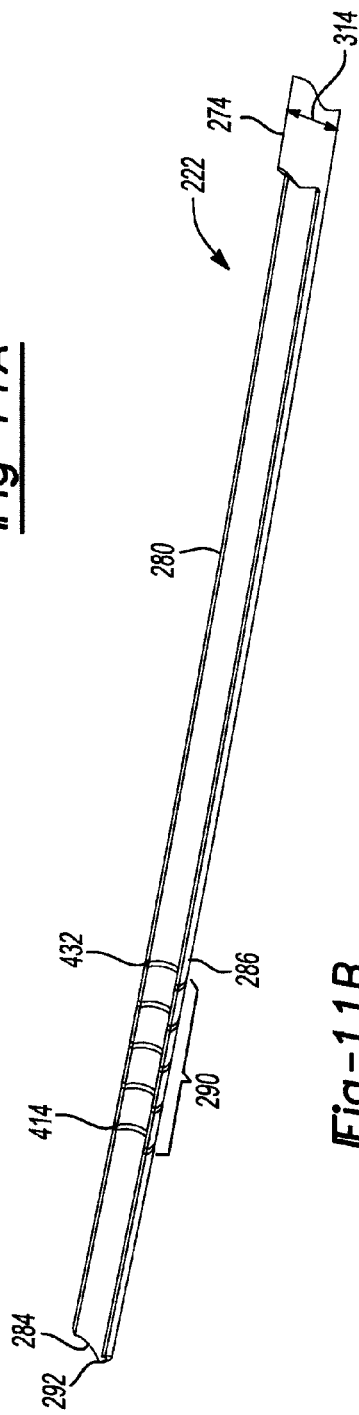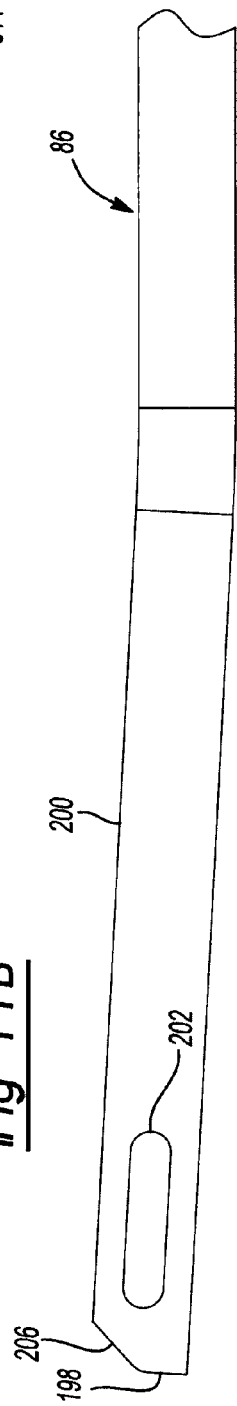

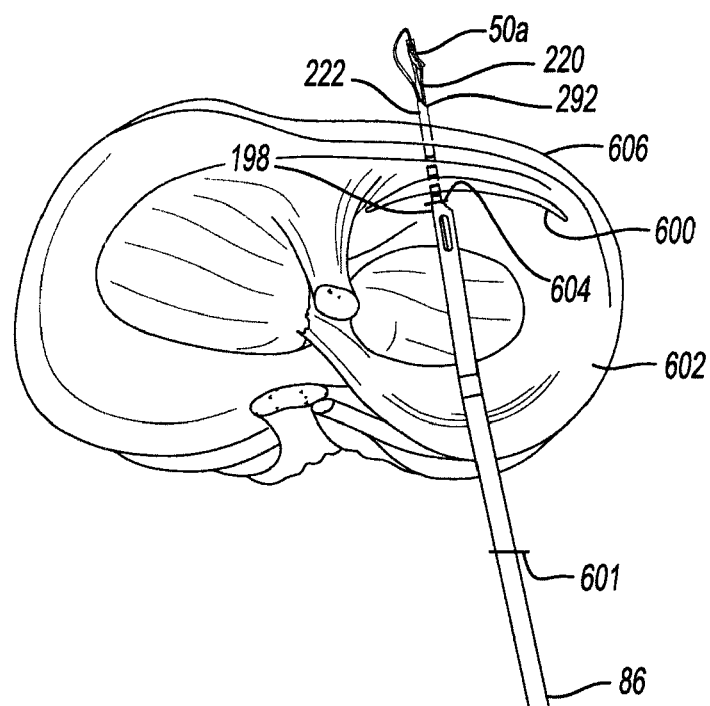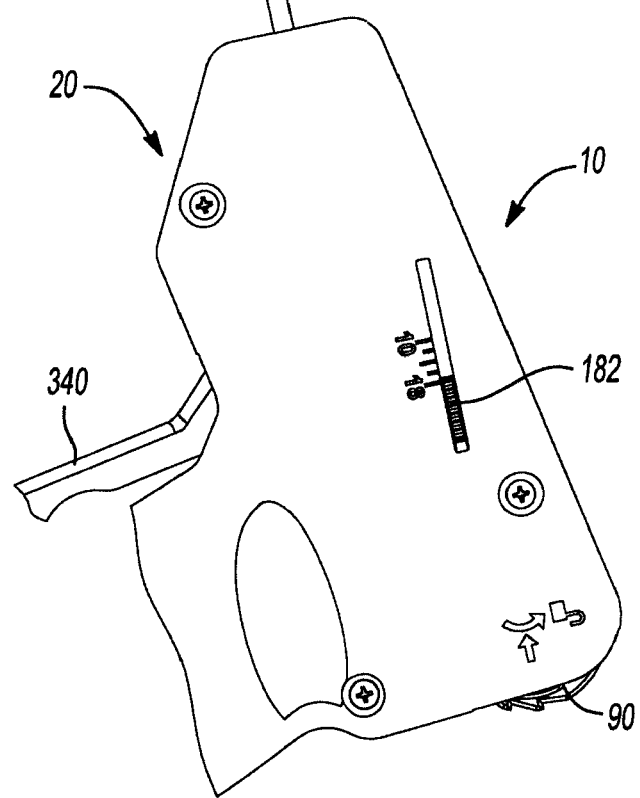
Fig-21

SOFT TISSUE REPAIR DEVICE AND METHOD

CROSS-REFERENCE TO RELATED APPLICATIONS

This application is a continuation-in-part application of U.S. patent application Ser. No. 12/489,181 filed Jun. 22, 2009, which is a continuation-in-part application of U.S. patent application Ser. No. 12/474,802 filed on May 29, 2009 (now U.S. Pat. No. 8,088,130), which is a continuation-in-part application of U.S. patent application Ser. No. 11/541,506 filed on Sep. 29, 2006 (now U.S. Pat. No. 7,601,165), and is a continuation-in-part application of U.S. patent application Ser. No. 11/541,505 filed on Sep. 29, 2006 (now U.S. Pat. No. 7,658,751).

This application is a continuation-in-part application of U.S. patent application Ser. No. 12/014,399 filed on Jan. 15, 2008 (now U.S. Pat. No. 7,909,851), which claims the benefit of U.S. Provisional Application No. 60/885,062, filed on Jan. 16, 2007, and of U.S. Provisional Application No. 60/885,057, filed on Jan. 16, 2007.

This application is a continuation-in-part application of U.S. patent application Ser. No. 12/014,340 filed on Jan. 15, 2008 (now U.S. Pat. No. 7,905,904), which is a continuation-in-part application of U.S. patent application Ser. No. 11/935,681 filed on Nov. 6, 2007 (now U.S. Pat. No. 7,905,903), and is a continuation-in-part application of 11/869,440 filed on Oct. 9, 2007 (now U.S. Pat. No. 7,857,830), which is a continuation-in-part of U.S. patent application Ser. No. 11/408,282 filed on Apr. 20, 2006, and now abandoned, and is a continuation-in-part application of 11/784,821 filed on Apr. 10, 2007, and is a continuation-in-part application of 11/347,661 filed on Feb. 3, 2006 (now U.S. Pat. No. 7,749,250), and is a continuation-in-part application of 11/347,662 filed on Feb. 3, 2006, and now abandoned, which is a continuation-in-part of U.S. patent application Ser. No. 10/983,236 filed on Nov. 5, 2004, and now abandoned.

This application is also a continuation-in-part of U.S. patent application Ser. No. 12/489,168 filed Jun. 22, 2009, which is a continuation-in-part of U.S. patent application Ser. No. 12/196,405 filed on Aug. 22, 2008 now U.S. Pat. No. 8,128,658, and a continuation-in-part of U.S. patent application Ser. No. 12/196,407 filed on Aug. 22, 2008 now U.S. Pat. No. 8,137,382, and is a continuation-in-part of U.S. patent application Ser. No. 12/196,410, filed on Aug. 22, 2008 (now U.S. Pat. No. 8,118,836).

FIELD

The present teachings relate generally to soft tissue repair and, more particularly, to a device and associated method for repairing a tear in soft tissue.

INTRODUCTION

Tears caused by trauma or disease in soft tissue, such as cartilage, ligament, or muscle, can be repaired by suturing. Various repair devices have been developed for facilitating suturing and are effective for their intended purposes. Nevertheless, tissue repair devices for facilitating suturing are still desirable.

SUMMARY

This section provides a general summary of the disclosure, and is not a comprehensive disclosure of its full scope or all of its features.

According to one aspect, the present teachings provide a soft tissue repair device. The device can include a housing having a handle, a deployment system having an actuation member, and an insertion system having an inserter and a slider. The slider can be coupled to the actuation member and movable relative to the inserter between deployed and retracted positions. At least a portion of a first anchor can be carried on an external surface of the slider in a first position, and at least a portion of a second anchor can be carried on the external surface of the slider in a second position that is longitudinally spaced apart from the first anchor position such that the portions of the first and second anchors are co-axial with the slider and each other. A flexible strand can couple the first and second anchors. The insertion system can be operable to cooperate with the deployment system to move the slider from the retracted position to the deployed position to deploy the first anchor upon actuating the actuation member at a first time, and to move the slider from the retracted position to the deployed position to deploy the second anchor upon actuating the actuation member a second time after the first time.

According to another aspect, the present teachings provide a method for repairing a tear in soft tissue. The method can include coupling first and second flexible anchors with a flexible strand, providing an insertion device having a housing with a pistol grip handle, an inserter and a slider carried in the inserter such that the inserter and the slider each have a distal end extending from the housing. The first and second coupled anchors can be loaded on an external surface of the slider, and the inserter can be inserted though the soft tissue from a first side of the tear to a second side of the tear. An actuation member protruding from the pistol grip handle can be actuated at a first time to translate a distal end of the slider beyond a distal end of the inserter so as to deploy the first anchor. The actuation member can be released after deploying the first anchor, the inserter can be inserted through the soft tissue for a second time in a second position, and the actuation member can be actuated at a second time after the first time to extend the distal end of the slider beyond the distal end of the inserter and deploy the second anchor. The method can further include removing the inserter from the soft tissue, tensioning the flexible strand and reducing the tear.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description, the appended claims and the following drawings. The drawings are for illustrative purposes only and are not intended to limit the scope of the present disclosure.

FIG. 11A is a partial exploded perspective view of the carrying wire of FIG. 11 having a pair of pre-loaded anchors according to the present teachings;

FIG. 11B is a partial exploded perspective view of the insertion member of FIG. 11 according to the present teachings;

FIG. 11C is a partial exploded perspective view of the outer cannula of FIG. 11 according to the present teachings;

FIG. 21 is an exemplary environmental view showing a first anchor being deployed outside of soft tissue according to the present teachings;

DESCRIPTION OF VARIOUS ASPECTS

Figure 1:
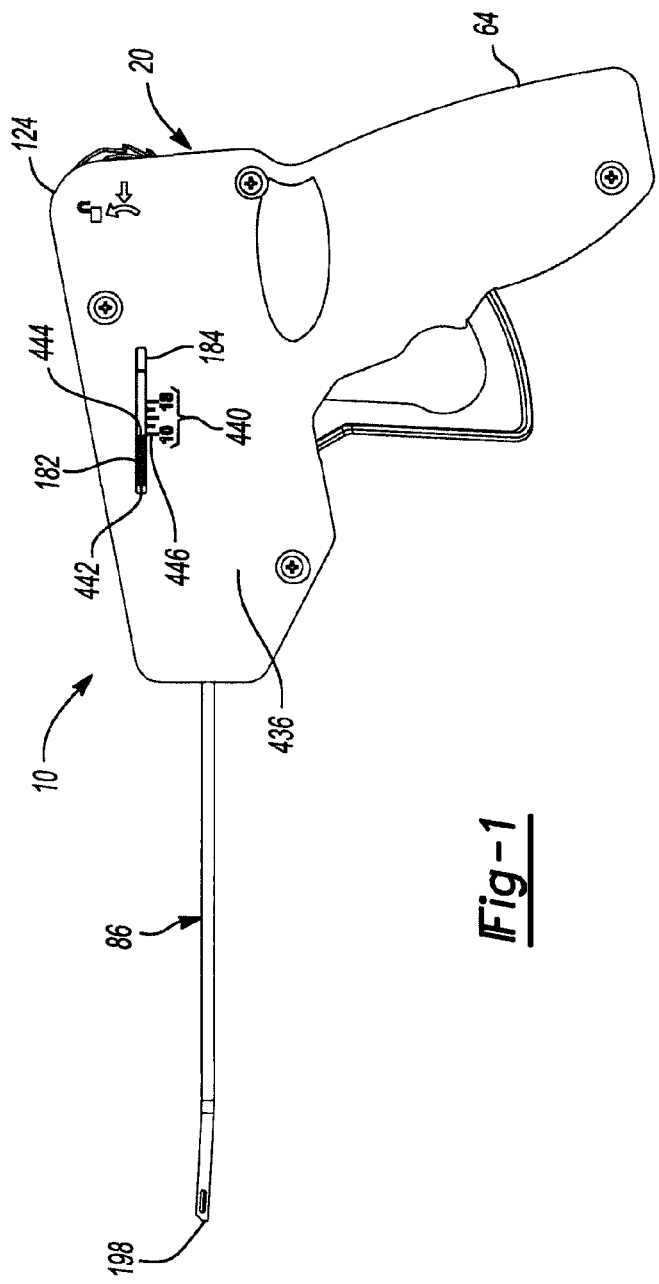
FIG. 1 is a side view of an exemplary tissue repair device according to the present teachings.

The following description is merely exemplary in nature and is in no way intended to limit the present disclosure, its application, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone.

With initial reference to FIGS. 1-6, an exemplary tissue repair device 10 according to the present teachings is illustrated. As will be further described below, the device 10 can include a casing 20 housing a depth limiting or positioning system 30 that cooperates with an insertion system 40, which can be preloaded with one or more flexible suture anchors 50 configured to be delivered into soft tissue. Two flexible suture anchors 50 are illustrated in various Figures, including FIG. 6, and will be generally referred to hereinafter as first and second flexible anchors 50a, 50b for clarification purposes. The casing 20 can include a two-part casing having a first half portion 60 arranged to engage a second half portion 62, such that together the half portions 60, 62 can form a pistol grip handle portion 64. Each casing portion 60, 62 can include a proximal end 66, a distal end 68, a top 70 and a bottom 72 generally located at a distal end of pistol grip handle portion 64. Casing 20 can be formed from plastic or any other suitable material.

The depth positioning system 30 can include a rotatable cam member 80, an axially moving translation member 82, a biasing member 84, and an axially moveable outer cannula 86. With continuing reference to FIGS. 1-6 and additional reference to FIGS. 7-9B, cam member 80 can include a thumbwheel 90 having a first side 92, a second side 94 and an outer periphery 96. The first side 92 can include a central first projection or post 98 extending from a center thereof that can be positioned in a corresponding slot 100 in first casing portion 60. In a similar manner, second side 94 can likewise include a central second projection or post 104 extending therefrom in an opposite direction as post 98 and can be positioned in a corresponding slot 108 in second casing portion 62. Slots 100, 108 can have a longitudinal length greater than a diameter of respective posts 98, 104 so as to provide for both translation and rotation of thumbwheel 90, as will be described in greater detail below.

Thumbwheel 90 can further include a toothed portion 114 disposed around a portion of outer periphery 96 and configured to be engagable by a user of the device 10. Casing portions 60, 62 can each include respective recesses 118, 120 that together form an opening 122 to facilitate a portion of thumbwheel 90 extending through the opening 122 and beyond a periphery 124 of casing 20, as shown for example in FIGS. 1 and 3. First side 92 can further include a first rotation limiting surface 130, a first cam surface 132 positioned adjacent thereto, and second and third rotation limiting surfaces 134 and 136, respectively, the operation of which will be described in greater detail below. A recess area 138 can be formed in outer periphery 96 so as to provide access to surfaces 130-136.

The toothed portion 114 can include a plurality of teeth 140 with each tooth having an inclined or ramped surface 142 that mates with second surface 144 orientated generally normal to the outer periphery 96 of thumbwheel 90. The ramped surfaces 142 can be orientated such that they incline away from the outer periphery in a counter-clockwise direction shown by arrow A in FIG. 3.

Figure 2:
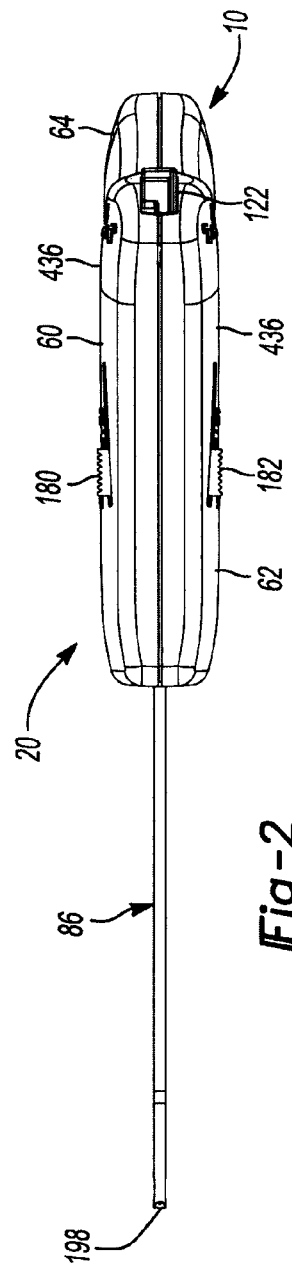
FIG. 2 is a top view of the exemplary tissue repair device according to the present teachings.
Figure 3:
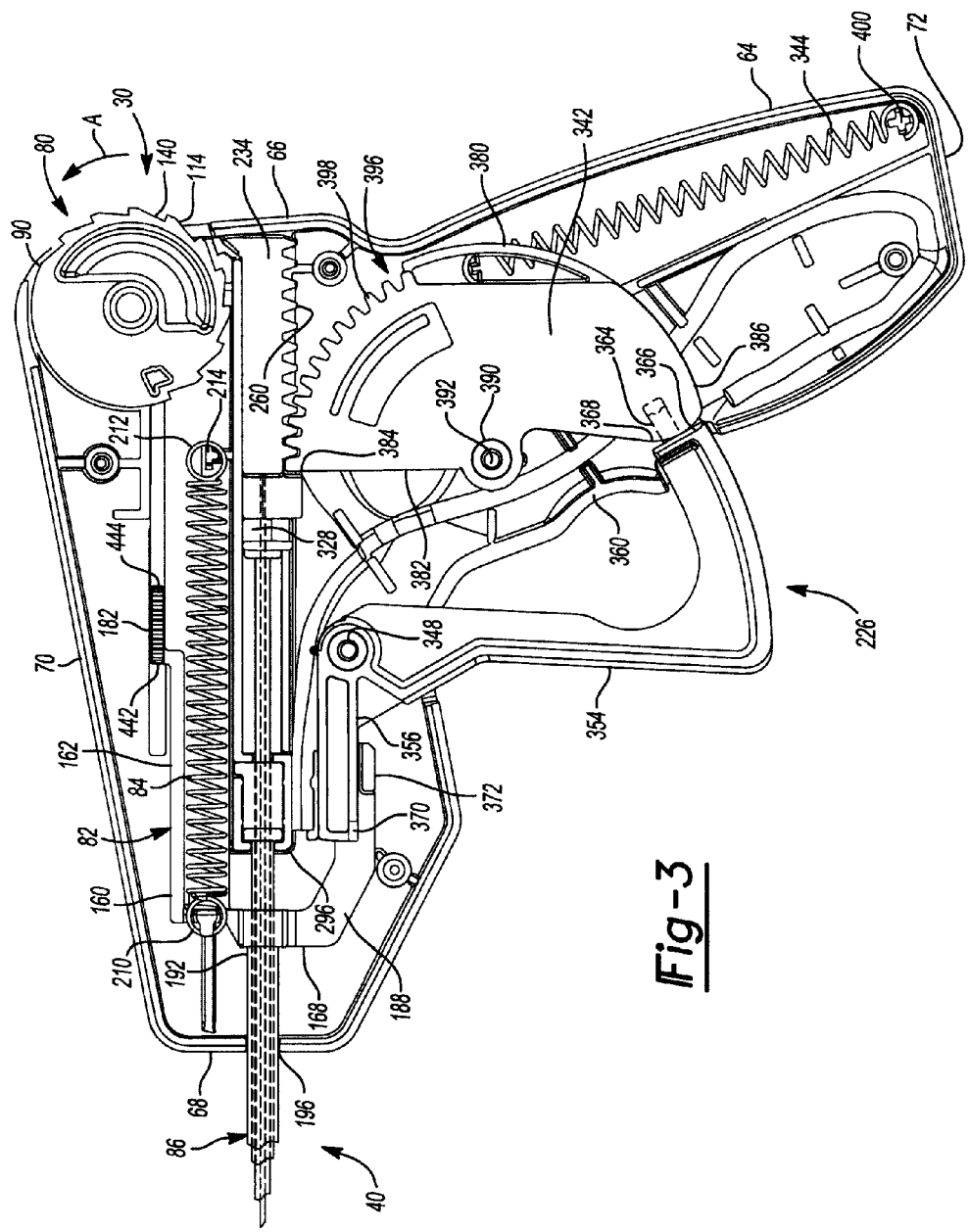
FIG. 3 is a partial side view of an exemplary configuration of the tissue repair device shown with a portion of the casing removed according to the present teachings.
Figure 4:
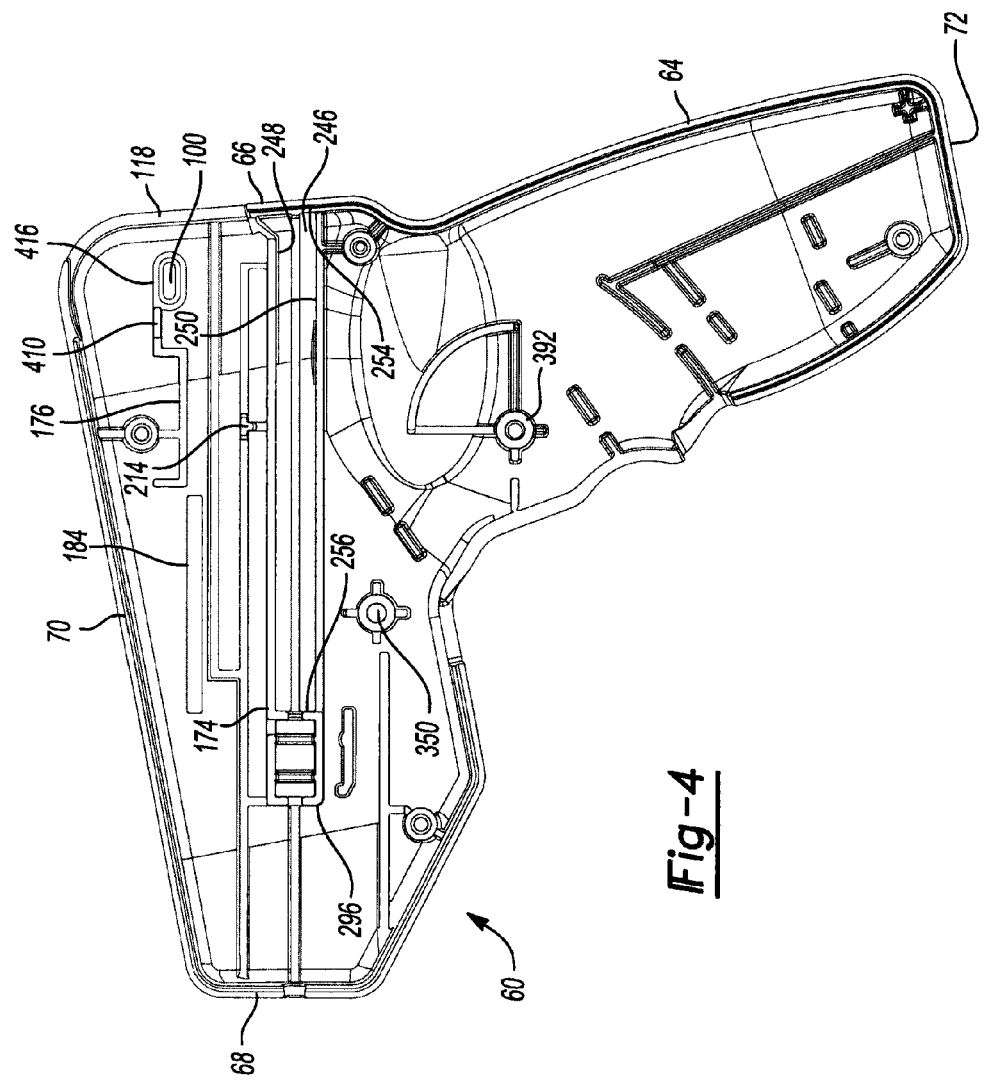
FIG. 4 is a side view of a portion of the casing of the device of FIG. 1 according to the present teachings.
Figure 5:
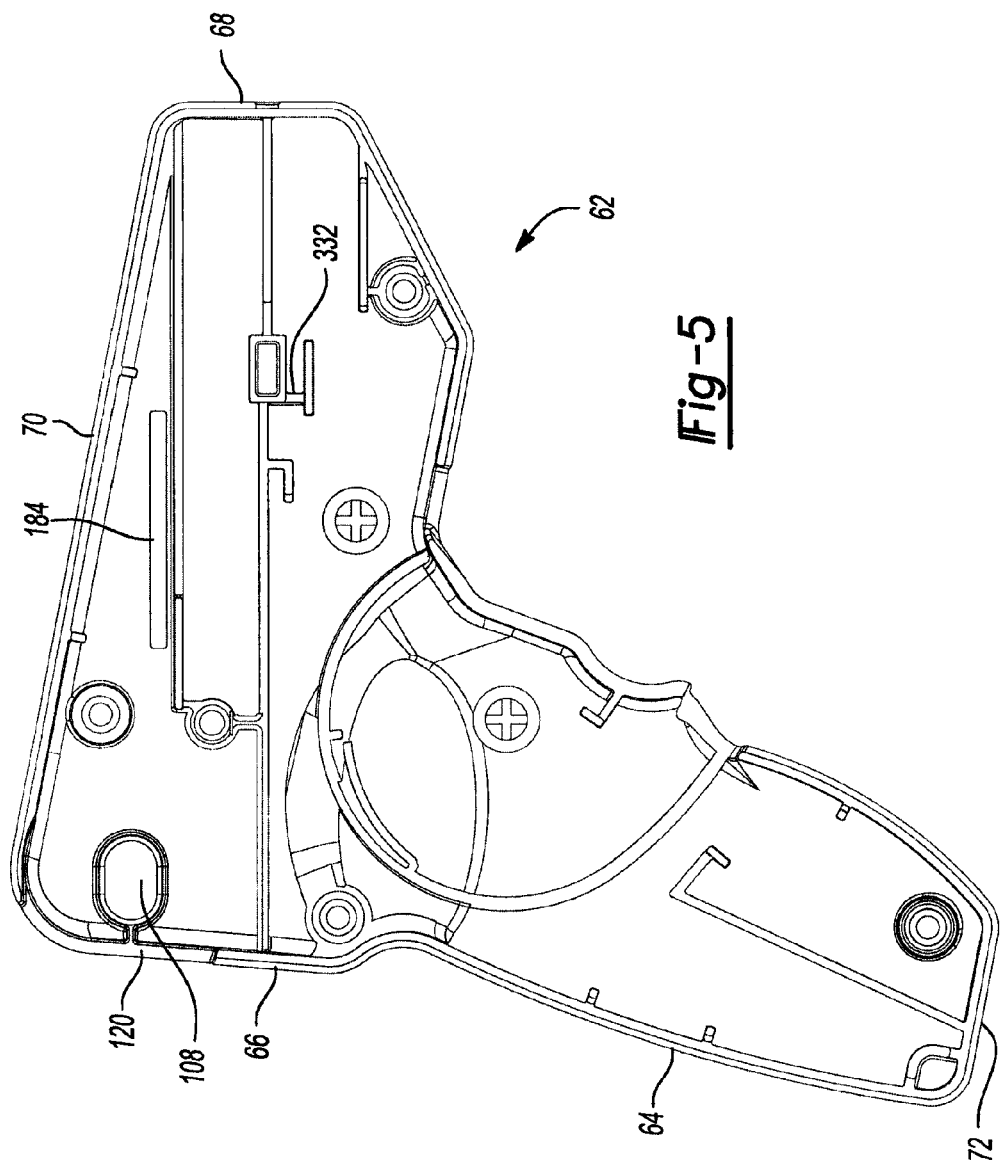
FIG. 5 is a side view of another portion of the casing of the device of FIG. 1 according to the present teachings.
Figure 6:
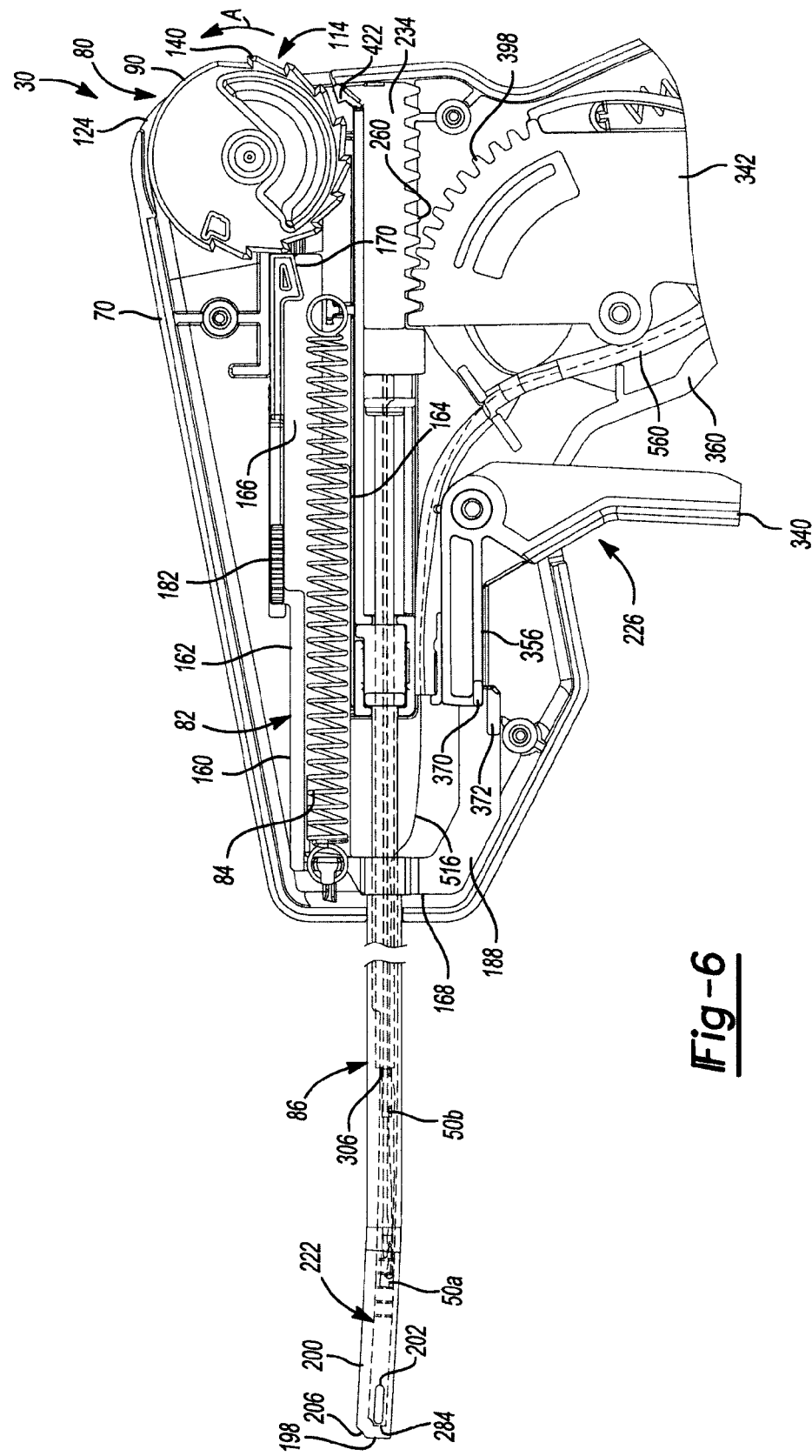
FIG. 6 is a partial side view of the device of FIG. 1, shown in an exemplary configuration according to the present teachings.

Translation member 82 can include a longitudinally extending portion 160 having a top 162, a bottom 164, a side portion 166 connecting the top and bottom 162, 164, a distal end 168 and a proximal end 170, as shown for example in FIG. 6. Translation member 82 can be positioned in casing 20 such that bottom 164 is adjacent a flange portion 174 of first casing portion 60 and top 162 is adjacent a flange portion 176 also of first casing portion 60, as generally shown in FIG. 4 with reference to FIG. 6. Flange portions 174, 176 can form a channel that guides translation member 82 during translation. A pair of position indication members 180, 182 can extend transversely in opposite directions from top 162 so as to extend through slots 184 in respective casing portions 60, 62 as shown in FIGS. 1 and 2.

Translation member 82 can further include an L-shaped portion 188 extending from distal end 168, as shown for example in FIG. 6. A proximal end 192 of outer cannula 86 can be coupled to L-shaped portion 188 such that outer cannula 86 can slidably protrude through an aperture 196 formed by casing portions 60, 62. A distal end 198 of outer cannula 86 can include a curved or inclined portion 200 as well as a pair of elongated apertures 202 positioned in alignment on opposite sides of cannula 86, as shown for example in FIG. 11C. Outer cannula 86 can also include a beveled or chamfered end 206 at a distal most end thereof adjacent to apertures 202. Chamfered end 206 can include a rounded or smooth end for placement adjacent to or abutting tissue without piercing the tissue. It should be appreciated that distal end 198 of outer cannula 86 can also be straight or non-inclined, arcuate, angled, etc. depending on a desired use or application, and can also be provided with or without apertures 202 and chamfered end 206.

Biasing member 84 can be connected at a first end 210 to the distal end 168 of translation member 82 and at a second end 212 to a tab 214 fixed to first casing portion 60. Biasing member 84 can be any suitable device, such as a coil spring, configured for expanding and contracting while also exerting a biasing force that biases the proximal end 170 of translation member 82 into engagement with thumbwheel 90.

Figure 10:
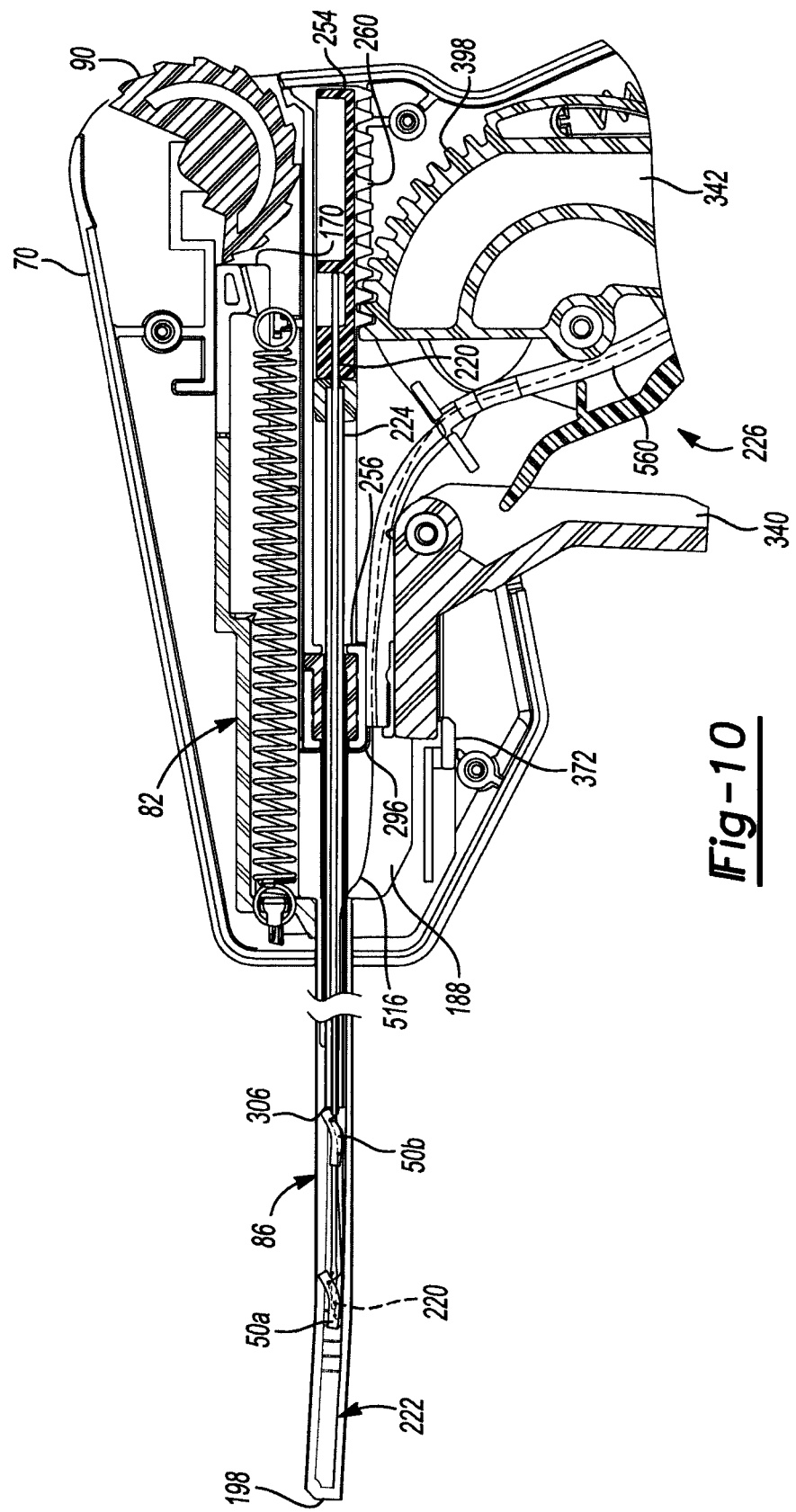
FIG. 10 is a partial sectional view of the device of FIG. 1, shown in an exemplary configuration according to the present teachings.
Figure 11:
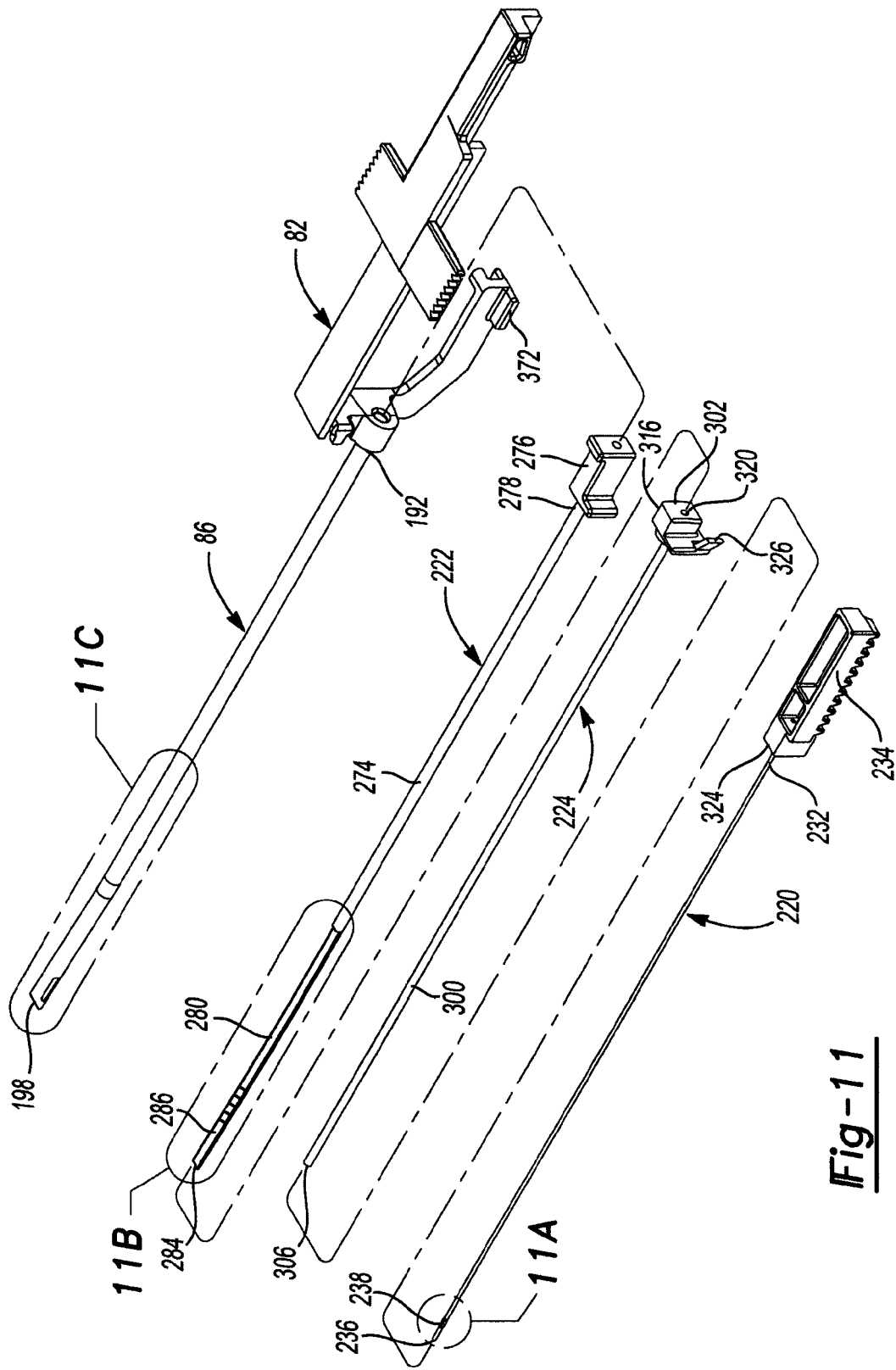
FIG. 11 is an exploded perspective view of an exemplary carrying wire, positioning member, insertion member and outer cannula of the device of FIG. 1 according to the present teachings.
Figure 12:
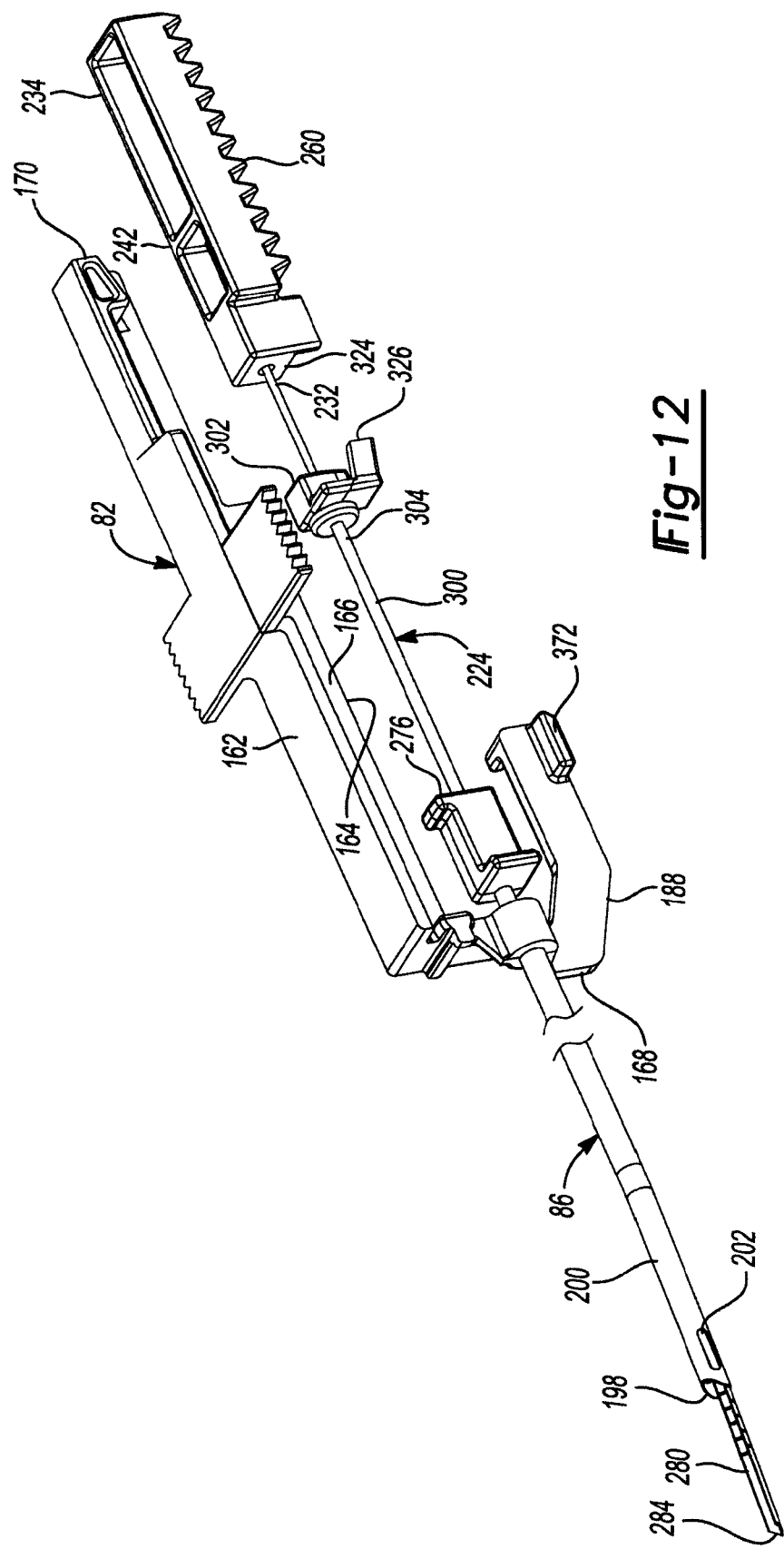
FIG. 12 is a perspective view of the components of FIG. 11, shown in an exemplary assembled configuration according to the present teachings.
Figure 13:
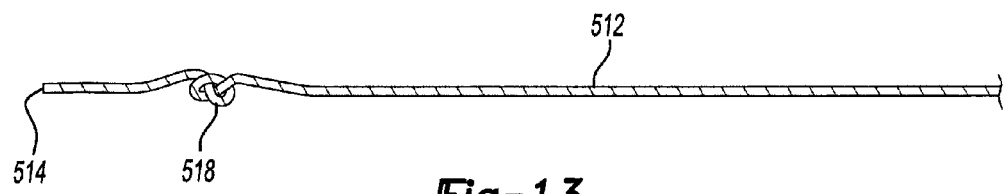
FIGS. 13, 14, 15 and 17 are sequential views illustrating an exemplary method and arrangement for coupling first and second flexible anchors with a flexible strand.
Figure 14:
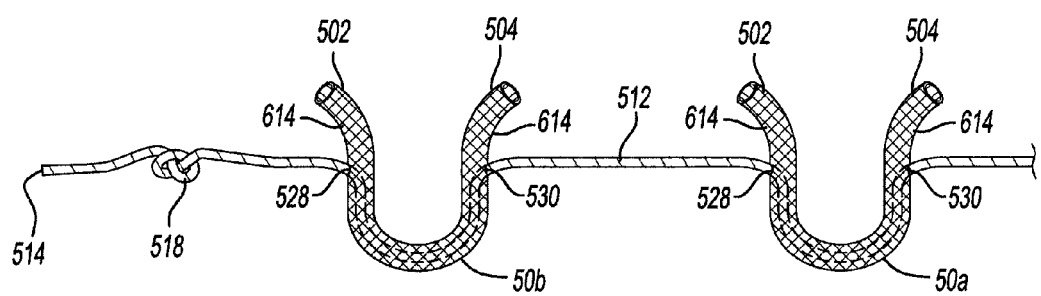

With additional reference to FIGS. 10-12, the insertion system 40 will now be described. Insertion system 40 can include a slider or carrying wire 220, an insertion member 222, a loading or positioning member 224, and a deployment system 226. Carrying wire 220 can include a solid, semi-rigid construction 230 with a proximal end 232 fixedly coupled to a cam follower 234 and a distal end 236 having a suture anchor engagement portion 238. Cam follower 234 can include a generally rectangular shape 242 that can be configured to translate in a track 246 defined by flanges 248 and 250 in first casing portion 60. Track 246 can further include proximal and distal ends 254 and 256 serving to limit travel of the cam follower 234 therebetween, as shown in FIGS. 4 and 10. A lower surface of cam follower 234 can include a plurality of gear teeth 260 configured for meshing engagement with a cam member 342 to translate carrying wire 220 between a stowed position where cam follower 234 abuts proximal end 254 and a deployed position where cam follower 234 abuts distal end 256, as will be further described below.

The insertion member 222 can include a tubular portion 274 extending from a body member 276 at a proximal end 278 and a trough portion 280 mating with the tubular portion 274 and extending therefrom to a distal end 284. The trough portion 280 can include an inclined portion 286 complimentary to the inclined portion 200 of cannula 86. It should be appreciated that insertion member 222 can be provided with a straight or non-inclined distal end that could correspond to a straight distal end of outer cannula 86. Inclined portion 286 can include depth indicator markers 290, as well as a pointed and chamfered distal most end 292 capable of piercing skin and soft tissue. Body member 276 can be configured for positioning in a correspondingly shaped cavity 296 to fix insertion member 222 relative to casing 20 and outer cannula 86. The distal end 284 of insertion member 222 can be received in outer cannula 86 such that at least a portion of trough portion 280 and tubular portion 274 can reside within cannula 86 as shown for example in FIGS. 11 and 12.

The positioning member 224 can include a tubular portion 300 fixedly coupled to an engagement member 302 at a proximal end 304, and a distal end 306 configured to engage suture anchor 50b, as will be described in greater detail below in connection with the operation of device 10. Tubular portion 300 can include an inside diameter larger than the suture engagement portion 238 of carrying wire 220 but an outside diameter less than an inside diameter 314 of insertion member 222. Engagement member 302 can include a generally square or rectangular shape 316 configured to mate with the dimensions of track 246 such that engagement member 302 can be slidably received within track 246. Tubular portion 300 can be slidably received within the tubular portion 274 of insertion member 222 such that distal end 306 and a portion of tubular portion 300 are slidably housed within insertion member 222, as shown in FIGS. 11 and 12.

Figure 19:
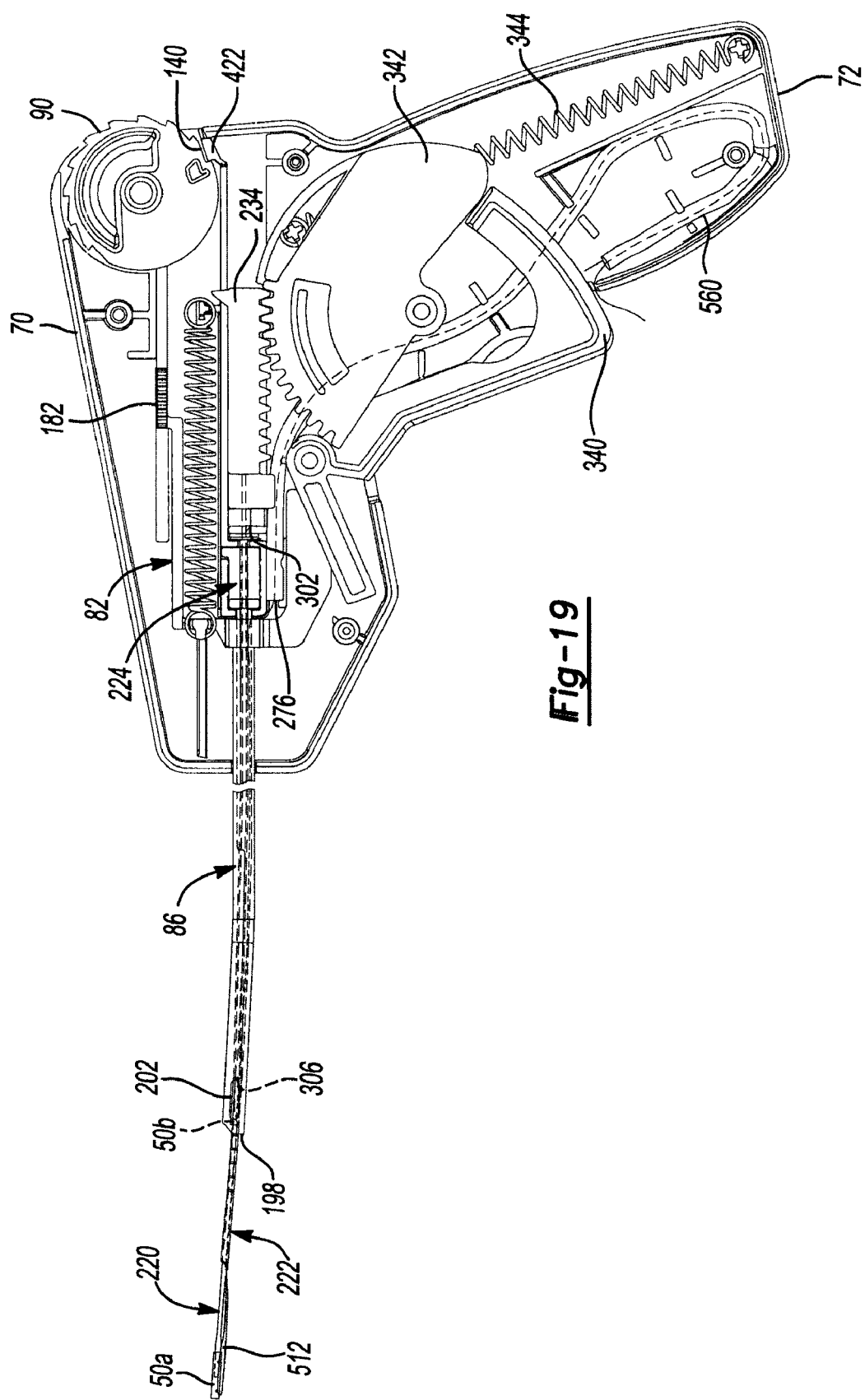
FIG. 19 is a partial side view of the device of FIG. 1, shown in an exemplary configuration according to the present teachings.

Carrying wire 220 can be inserted through positioning member 224 via aperture 320 such that positioning member 224 can translate on and relative to carrying wire 220. With carrying wire 220 disposed through positioning member 224, engagement member 302 and cam follower 234 can be positioned in track 246 such that engagement member 302 abuts a distal end 324 of cam follower 234 when cam follower 234 is in the stowed position. A retention tab 326 can also extend from a top portion 328 of engagement member 302. Retention tab 326 can be configured to engage a flange 332 extending from casing portion 62 so as to retain engagement member 302 relative to flange 332 when cam follower 234 is translated to the deployed position, as shown in FIG. 19 with reference to FIGS. 5 and 12.

Deployment system 226 can include a trigger 340, a cam member 342 and a biasing member 344. Trigger 340 can include an aperture 348 for pivotally coupling trigger 340 to a pivot post 350 of first casing portion 60, a user engageable portion 354 and a flange member 356. User engageable portion 354 can protrude through an aperture 360 formed by respective casing portions 60, 62 so as to be accessible by a user, as will be further described below. A coupling member 364 can extend from an end 366 of trigger 340 that is configured to abut cam member 342 so as to engage and couple trigger 340 to an end 368 of cam member 342. Flange member 356 can extend from aperture 348 in a direction substantially orthogonal to user engageable portion 354. Flange member 356 can include a tab 370 protruding from a distal end thereof and configured to engage a corresponding tab 372 protruding from L-shaped portion 188, as shown for example in FIG. 6. When tabs 370 and 372 align, trigger 340 is locked such that it can not be rotated from the non-deployed position shown in FIG. 6.

Cam member 342 can include a generally semicircular shaped portion 380 and a generally planer portion 382 spanning between respective ends 384, 386 of portion 380. An aperture 390 can be centrally positioned between ends 384, 386 and configured to engage a pivot post 392 protruding from first casing portion 60 such that cam member 342 can pivot about post 392. Arcuate portion 380 can include a portion 396 having a plurality of gear teeth 398 adjacent to and configured for meshing engagement with the plurality of gear teeth 260 of cam follower 234. Biasing member 344 can be coupled at one end to a retention tab proximate arcuate portion 380 and at another end to a retention post 400 protruding from first casing portion 60. Biasing member 344 can include a coil spring or other device suitable for imparting a biasing force onto cam member 342 to bias trigger 340 to the non-deployed position, as shown for example in FIG. 6.

Figure 20:
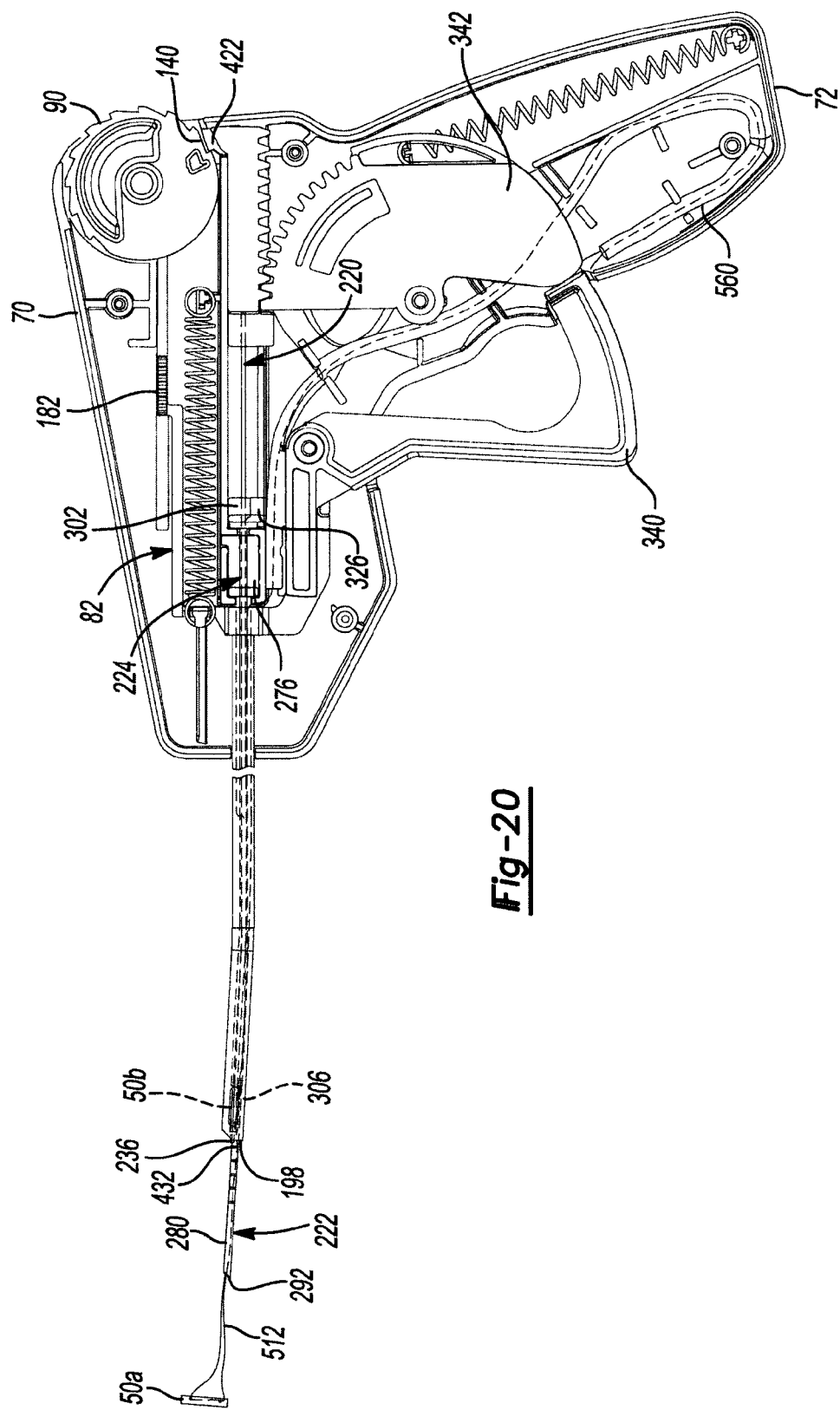
FIG. 20 is a partial side view of the device of FIG. 1, shown in another exemplary configuration according to the present teachings.

User engageable portion 354 of trigger 340 can be grasped by a user and squeezed or depressed so as to rotate trigger 340 about pivot post 350. Upon such rotation, trigger end 366 can drive cam member 342 to rotate about pivot post 392, which in turn will drivingly engage cam member gear teeth 398 with cam follower gear teeth 260 and translate cam follower 234 and carrying wire 220 forward from the stowed position to the deployed position, as generally shown in FIG. 19. Upon the user releasing trigger 340, the biasing force exerted by biasing member 344 can return cam follower 234, cam member 342 and trigger 340 to the non-deployed positions, as generally shown in FIGS. 6 and 20.

Returning to FIGS. 6-9B, operation of the depth positioning system 30 in connection with the insertion system 40 and trigger lock feature will now be described in greater detail. Thumbwheel 90 can be used to adjust a position of the outer cannula 86 relative to casing 20 and insertion member 222. More specifically, outer cannula 86 can be axially adjusted from a sheathed position to several use positions such that insertion member 222 extends at predetermined lengths relative to distal end 198 of outer cannula 86.

Figure 9A:
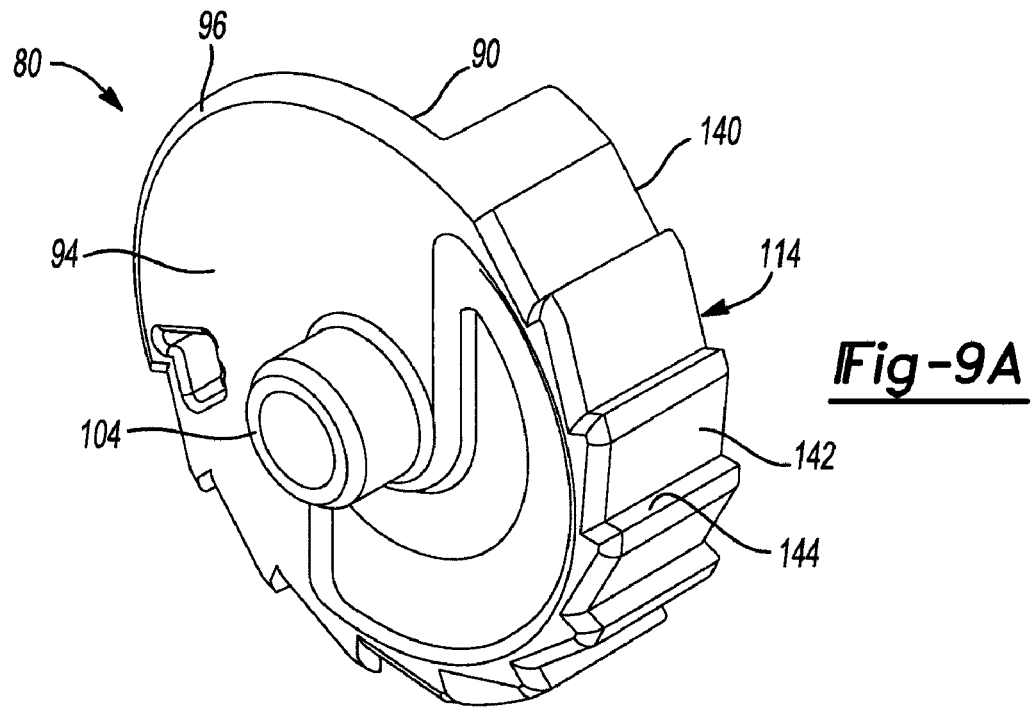
FIGS. 9A and 9B are perspective views of a cam member of the device of FIG. 1 according to the present teachings.
Figure 9B:
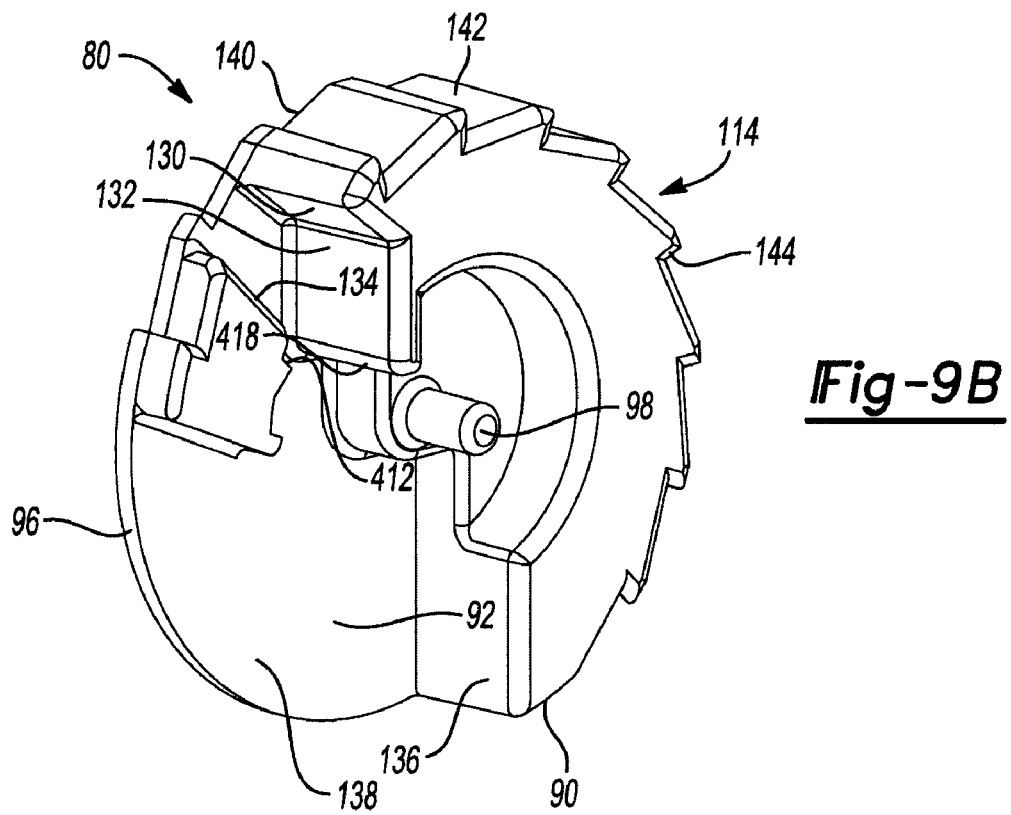

In the sheathed position, thumbwheel 90 can be positioned such that an engagement tab 410 protruding from first casing portion 60 is positioned between a projecting member 412 of rotation limiting surface 134 and an edge 418 of cam surface 132, as generally shown in FIG. 9B with reference to FIG. 4. In this position, thumbwheel 90 can be prevented from rotating and can engage the distal end of translation member 82 at the outer periphery 96 thereby positioning outer cannula 86 to a fully deployed or sheathed position, as shown in FIG. 6. In the sheathed position, outer cannula 86 can fully cover insertion member 222, carrying wire 220 and positioning member 224, as also shown in FIG. 6.

Figure 7:
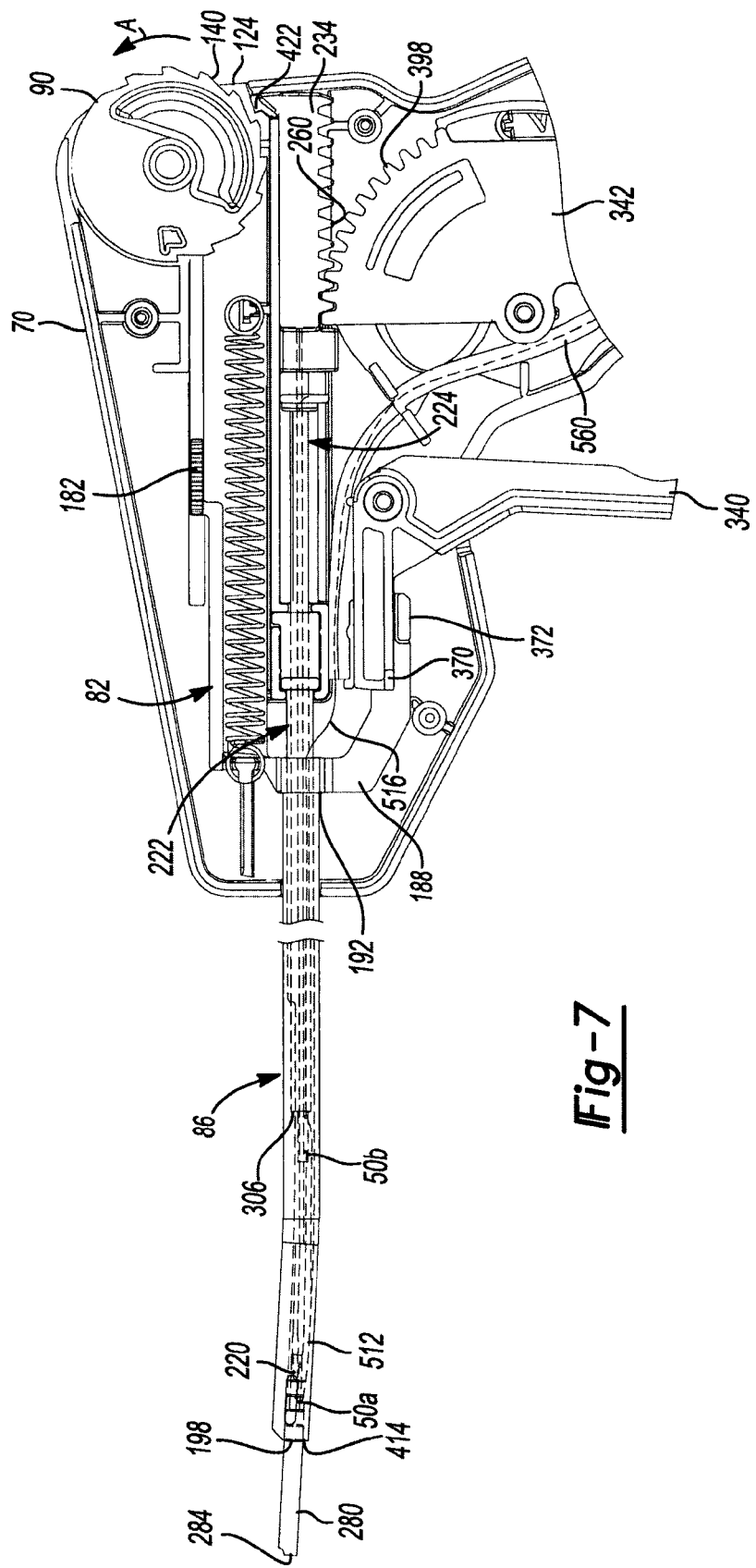
FIG. 7 is a partial side view of the device of FIG. 1, shown in another exemplary configuration according to the present teachings.

To move the depth positioning system 30 from the sheathed position to an initial use position, a user can push thumbwheel 90 to linearly translate thumbwheel 90 forward towards distal end 68 such that posts 98, 104 slide and translate forward in their respective slots 100, 108 and projection member 412 is disengaged from tab 410. Upon disengagement, thumbwheel 90 can be rotated counter-clockwise in the direction of arrow A such that recessed area 138 is now aligned with the proximal end 170 of translation member 82, as shown in FIG. 7. Biasing member 84 can then urge translation member 82 rearward into recess area 138 such that proximal end 170 engages first cam surface 132, as generally shown in FIG. 7 with additional reference to FIG. 9B. Cam surface 132 can be configured with a shape as shown that cooperates with proximal end 170 of translation member 82 and biasing member 84 to urge thumbwheel 90 to rotate in the direction of arrow A from the sheathed position to the initial use position. In the initial use position, the distal end 198 of outer cannula 86 can align with a first marker 414 of depth markers 290, and a tooth of the plurality of teeth 140 can engage a cooperating projection 422 of first casing portion 60, as also shown in FIG. 7.

Figure 8:
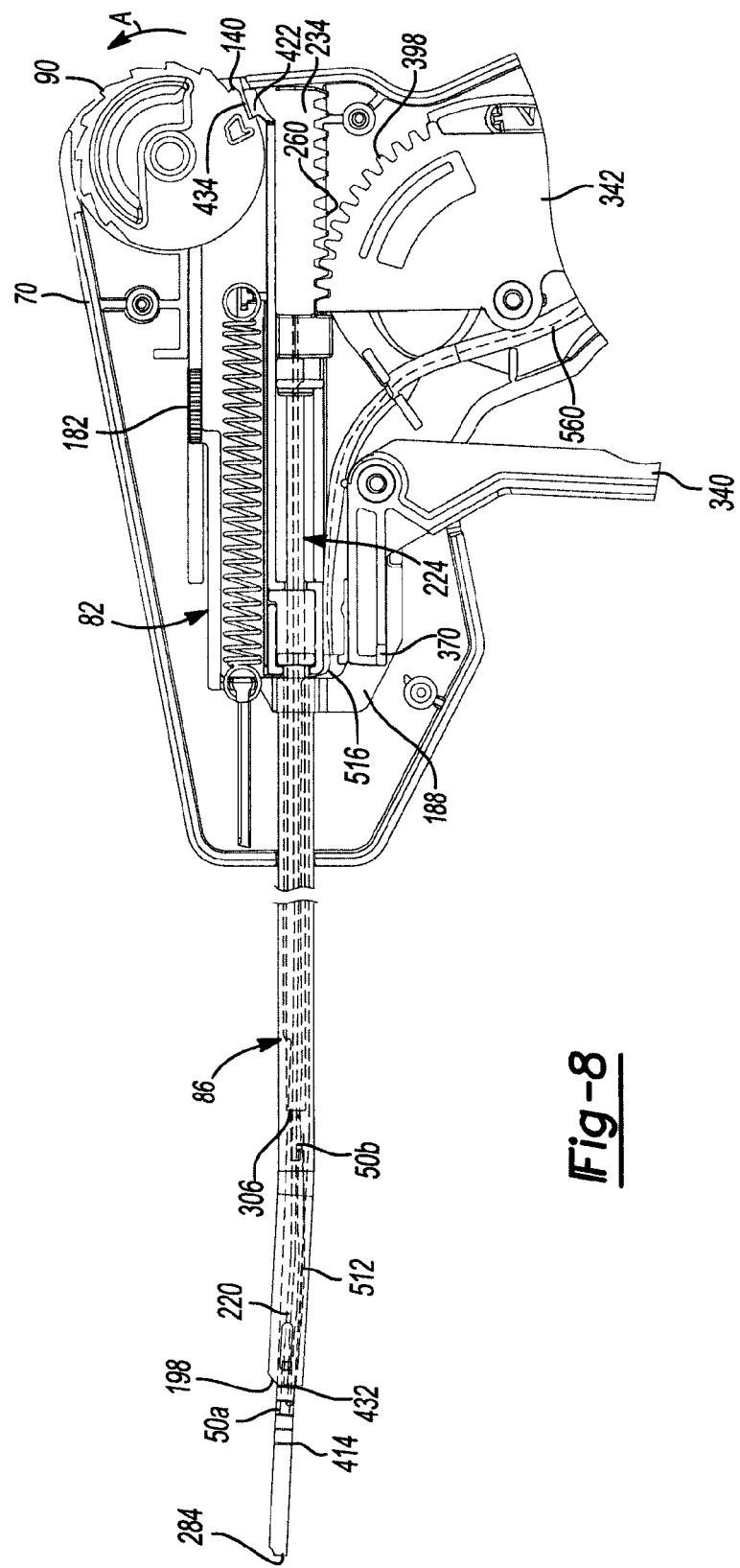
FIG. 8 is a partial side view of the device of FIG. 1, shown in another exemplary configuration according to the present teachings.

In the initial use position, outer cannula 86 can be partially translated rearward into casing 20 such that a distal end 284 of insertion member 222 is exposed. A user can now rotate thumbwheel 90 to adjust outer cannula 86 to a desired position relative to distal end 284 of insertion member 222. For example, a user could adjust outer cannula 86 relative to distal end 284 such that distal end 284 protrudes a predetermined distance that corresponds to a desired distance in which insertion member 222 can be inserted into the anatomy. In one exemplary configuration, thumbwheel 90 can be used to adjust outer cannula 86 relative to insertion member 222 by 8 millimeters in 2 millimeter increments from first marker 414 to fifth marker 432, as generally shown in FIG. 8. It should be appreciated that the depth and positioning system 30 can be configured to provide various amounts of adjustment as may be desired for various procedures. In this regard, thumbwheel 90 can include a plurality of discrete positions and/or infinite adjustment configurations as may be desired for various procedures.

With continuing reference to FIGS. 6-9B and additional reference to FIGS. 1 and 11B, depth markers 290 can be used to aid a user in positioning outer cannula 86 relative to insertion member 222. In an exemplary configuration, markers 290 and can include five discrete markers or indicia, with the first marker 414 corresponding to a distance of 10 millimeters from the distal end 284 of insertion member 222 to the distal end 198 of outer cannula 86. Each successive marker in a rearward direction towards casing 20 can be separated by 2 millimeters such that the fifth marker 432 can correspond to a distance of 18 millimeters from distal end 284 to distal end 198.

In addition, respective sides 436 of casing 20 can also include depth indicator markings or indicia 440, as shown in FIG. 1. Markings 440 can similarly include five markers that correspond to the same five positions as the markers 290 on insertion member 222. A distal side 442 of position indicator members 180, 182 can be configured to align with markings 440 to provide a visual indication on casing 20 of a position of the distal end 284 of insertion member 222 relative to outer cannula 86, as shown for example in FIG. 1. It should also be noted that when insertion system 40 is in the sheathed position, a proximal side 444 of position indicator members 180, 182 can align with a first marker 446 of markings 440, as shown in FIG. 1.

Each tooth of the plurality of teeth 140 on thumbwheel 90 can be correspondingly spaced apart such that thumbwheel 90 can be used to advance or retract outer cannula 86 in the 2 millimeter increments described above. More specifically, to retract outer cannula 86 away from distal end 284 of insertion member 222, thumbwheel 90 can be pressed forward, such that teeth surfaces 144 clear cooperating projection 422, and then rotated in the counter-clockwise direction of arrow A. For example, thumbwheel 90 can be translated forward and simultaneously rotated in the direction of arrow A to retract outer cannula 86 from the first marker 414 to the fifth marker 432 such that the distal end of insertion member 222 extends beyond outer cannula 86 by a distance of 18 millimeters, as shown in FIG. 8. In this position, second surface 144 adjacent an end of tooth 434 can engage cooperating projection 422 and rotation limiting surface 130 can engage surface 416 of first casing portion 60 adjacent engagement tab 410, as generally shown in FIGS. 8 and 9B. On the other hand, to advance outer cannula 86 towards distal end 284, thumbwheel 90 can be rotated in a direction opposite of arrow A with ramped surfaces 142 ratcheting against cooperating projection 422 to a desired position.

With reference to FIGS. 13-18, the flexible suture anchors 50a, 50b will now be described in greater detail. Each flexible anchor 50a, 50b can be an elongated member having first and second ends 502, 504. The first and second ends 502, 504 can be substantially perpendicular to the longitudinal axis of the flexible anchors 50a, 50b. The flexible anchors 50a, 50b can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The flexible anchors 50a, 50b can have any properties that allow the flexible anchors 50a, 50b to change shape. The flexible anchors 50a, 50b can be, for example, compliant, flexible, foldable, squashable, squeezable, deformable, limp, flaccid, elastic, low-modulus, soft, spongy, perforated or any other flexible member which can change shape. In some aspects, the flexible anchors 50a, 50b can be coated with biological or biocompatible coatings, and can also be soaked in platelets and other biologics, which can be easily absorbed by the flexible anchors 50a, 50b in particular when, for example, the flexible anchors 50a, 50b are made from spongy, absorbent material.

Figure 18:
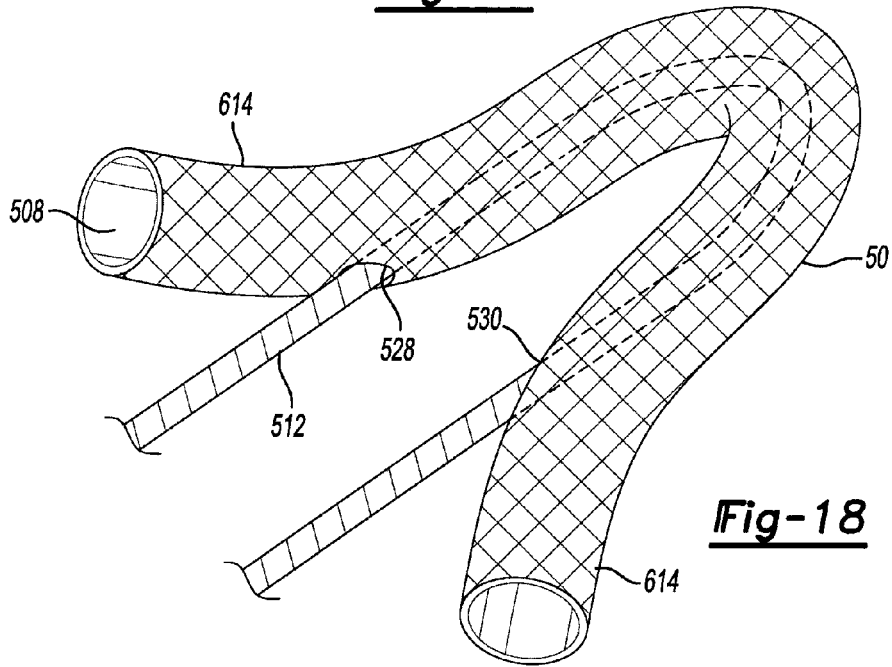
FIG. 18 is a perspective view of a flexible anchor coupled with a flexible strand according to the present teachings.

It should be understood by the above description that the flexible anchors 50a, 50b are not configured to pierce or otherwise penetrate tissue either with the first and second ends 502, 504, which are blunt or with any other portion thereof. The flexible anchors 50a, 50b can be loaded on the exterior of the distal end 256 of carrying wire 220, as will be discussed in greater detail below. The flexible anchors 50a, 50b can be in the form of an elongate flexible tube defining a bore 508 along their length, as shown in FIG. 18.

The first and second flexible suture anchors 50a, 50b can be coupled together with a flexible suture or strand 512. The flexible strand 512 can have first and second ends 514, 516 and can be made of braided filaments or fibers of biocompatible material, including natural and synthetic fibers, such as cotton, silk, polymer, polyester, polyethylene, thin wire, suture, and other materials. The flexible strand 512 can be braided in a tubular or hollow form such that it forms an internal passage 520 between the first and second ends 514, 516.

A small knot or other retaining device 518 can be optionally formed adjacent the first end 514. The flexible strand 512 can be passed through a first opening 528 of each of the flexible anchors 50a, 50b, guided along the corresponding bore 508 and passed through a second opening 530 of each flexible anchor 50a, 50b, as for example shown in FIG. 18. The openings 528, 530 can be positioned intermediately between the first and second ends 502, 504 of each flexible anchor 50a, 50b at a distance of, for example, one-quarter length from the ends 502, 504 of each flexible anchor 50a, 50b. Furthermore, it will be appreciated that the openings 528, 530 can be apertures or voids in the woven fabric of the flexible anchors 50a, 50b, such that the openings 528, 530 do not disrupt or break the weave of flexible anchors 50a, 50b, when the flexible anchor 50a, 50b are made of braided or woven material.

Figure 15:
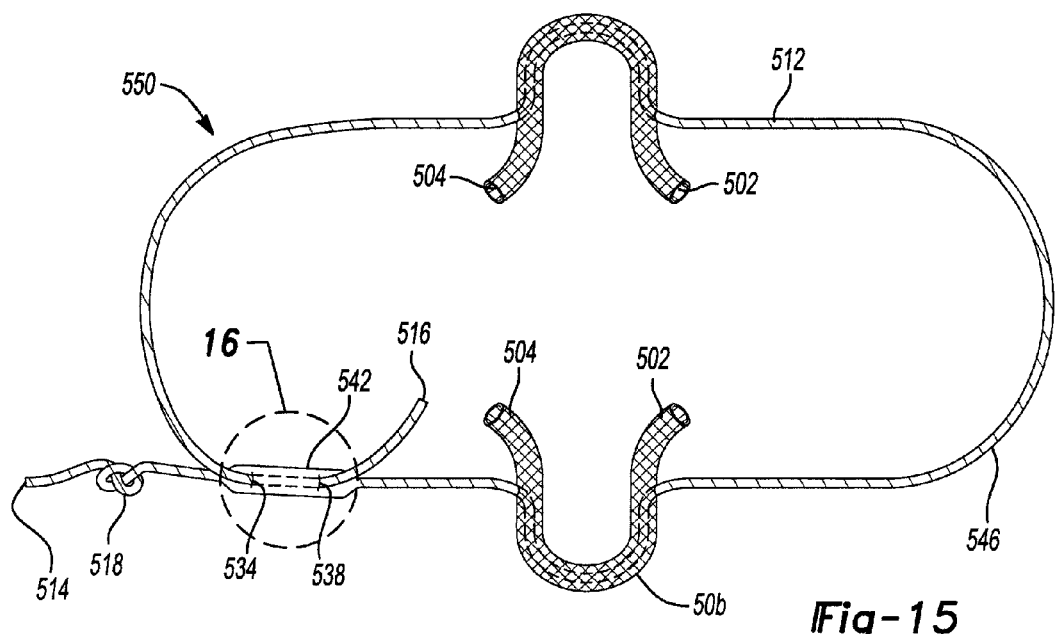
Figure 16:
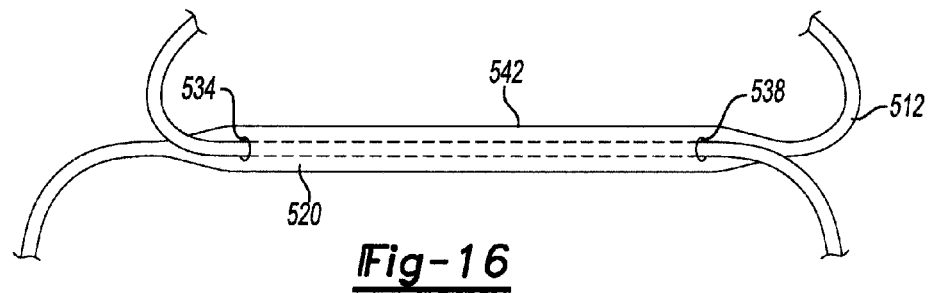
FIG. 16 shows a detail of FIG. 15 according to the present teachings.
Figure 17:
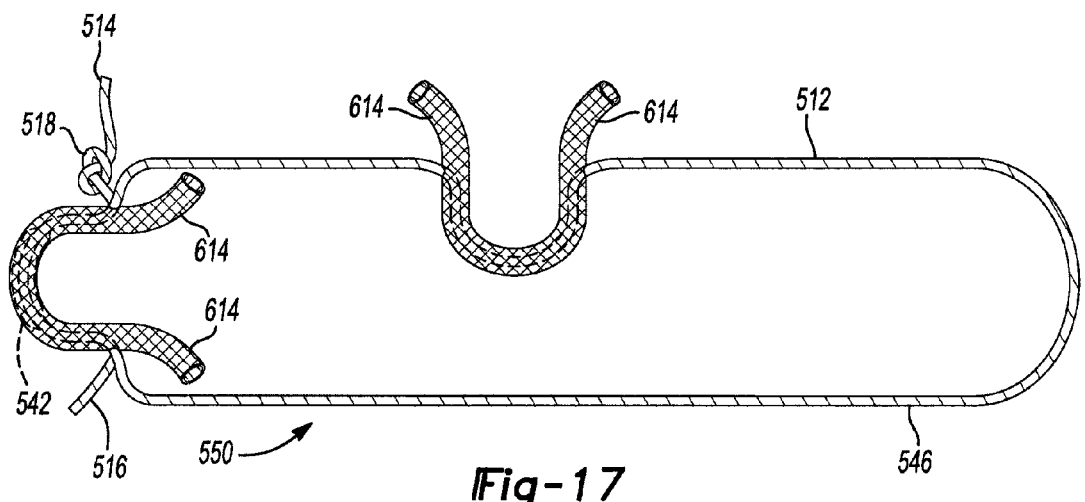

After the flexible anchors 50a, 50b are mounted on the flexible strand 512, the second end 516 of the flexible strand 512 can be inserted into the internal passage 520 of the flexible strand 512 at an aperture 534, guided longitudinally along the passage 520, and led out of the passage 520 of the flexible strand 512 at an aperture 538. The portion of the strand 512 between apertures 534 and 538 can form an adjustment portion 542 between the optional knot 518 and the opening 528 of the second flexible anchor 50b, such that the flexible strand 512 defines a single adjustable knotless loop 546, as shown in FIGS. 15 and 16. The second flexible anchor 50b can be slidably moved along the flexible strand 512 until the adjustment portion 542 is within the bore 508 of the second flexible anchor 50b and the knot 518 is adjacent the opening 528 of the second flexible anchor 50b, as shown in FIG. 17. It will be appreciated, however, that the adjustment portion 542 can remain in the position shown in FIG. 15 outside of bore 508. The adjustable knotless loop 546 is self-locking and does not require the surgeon to tie a knot during a surgical procedure for securing the flexible strand 512. Further, once the adjustable knotless loop 546 is self-locked by pulling the second end 516 of the flexible strand 512 and tensioning the flexible strand 512, friction prevents the adjustable knotless loop 546 from being loosened, thereby providing a secure lock. Additional details regarding forming the knotless adjustable loop 546, and additional adjustable knotless loop configurations are disclosed in co-pending and commonly assigned U.S. patent application Ser. No. 11/541,506, filed on Sep. 29, 2006, the disclosure of which is incorporated herein by reference.

For discussion purposes, the anchors 50a, 50b, together with flexible strand 512 configured in the knotless loop 546 can be hereinafter referred to as the anchor system 550. With reference to FIGS. 6 and 11A, the anchor system 550 can be pre-loaded in an in-line configuration on the carrying wire 220 such that anchor 50a is positioned before flexible anchor engagement portion 238 and second anchor 50b is positioned after engagement portion 238. In the in-line configuration, carrying wire 220 can extend through a portion of bore 508 of anchors 50a, 50b and then pierce though each anchor thereby creating a tail portion 548 that is not coaxial with carrying wire 220, as shown for example in FIG. 11A. In this configuration, the anchors 50a, 50b can reside in the trough portion 280 of insertion member 222. The flexible strand 512 can be packaged within outer cannula 86 along side insertion member 222 and positioning member 224. Second end 516 of flexible strand 512 can extend out of outer cannula 86 through aperture 196 and into a tubular housing member 560 positioned in a handle portion of first casing portion 60, as shown for example in FIG. 6.

Returning to FIGS. 11 and 11A, the suture anchor engagement portion 238 of carrying wire 220 will now be described in greater detail. Suture engagement portion can have a flattened area 580 having a thickness less than the outside diameter 312 of carrying wire 220. Flattened area 580 can be formed so as to maintain the same cross-sectional area as a cross section through a non-flattened portion of carrying wire 220, thereby providing for the suture anchors 50a, 50b to be sized relative to the diameter of carrying wire 220 while ensuring that they can slide over the engagement portion 238, as will be further described below.

The engagement portion 238 can further include a one-way barb 584 configured such that flexible anchors 50a, 50b can slide or travel over barb 584 in only one direction of travel from the proximal end 254 of carrying wire 220 to the distal end 236 thereof. One-way barb 584 can be defined by a recess or cut-out 588 formed in the flattened section such that a distal end 590 of an open end of recess 588 mates with a portion of flattened area 580 having a first width 592. A proximal end 594 of the recess 588 also adjacent the opening can mate with another portion of the flattened area 580 having a second width 598 greater than the first width 592. Flattened area 580 can also include curved transition areas 597, 599 between the flattened area 580 and a non-flattened area of the carrying wire on a proximal side thereof, as shown in FIG. 11A.

In use, the larger second width 598 of flattened area 580 and the angled nature of one-way barb 584 provides for suture anchor 50b to be able to slide or travel over the barb 584 in a proximal to distal direction without being caught or stopped by barb 584. In a similar manner, carrying wire 220 can slide or travel relative to suture anchor 50b in a distal to proximal direction without barb 584 catching or stopping flexible anchor 50b. Conversely, the smaller first width 592 of flattened area 580 in cooperation with barb 584 provides for catching an interior surface of bore 508 of suture anchor 50b when carrying wire 220 moves in a proximal to distal direction relative to flexible anchor 50b.

Referring now to FIGS. 6-8 and 19-23, the soft tissue repair device 10 pre-loaded with suture anchors 50a, 50b can be used to repair a soft tissue defect 600, such as, for example, a tear, or other weakness in fibrous soft tissue 602, such as in meniscal tissue, cartilage, muscle or other fibrous tissue under the skin. An outer incision 601 can be made through the skin to access the soft tissue 602 and a user can insert the distal end 198 of outer cannula 86 to the surgical site. An appropriate insertion depth can be determined for the insertion member 222 and the user can translate and rotate thumbwheel 90, as discussed above, to unlock the depth and positioning system 30 from the sheathed position to the initial use position. The outer cannula 86 can then be adjusted relative to insertion member 222 such that distal end 284 extends beyond outer cannula 86 a distance corresponding to the desired insertion depth.

The exposed distal end 284 of insertion member 222 can be inserted through first entry point 604 into soft tissue 602 from a first side of the defect 600 until the distal end 284 can exit a second side 606 of the fibrous soft tissue 602, such as an outer surface or back side of a meniscus of a knee joint or other outer surface of a fibrous tissue. In this position, the distal end 198 of outer cannula 86 can be adjacent to or abutting the first entry point 604. It should be appreciated that the chamfered end 292 of insertion member 222 could alternatively be used to pierce the skin without requiring an incision 604.

With distal end 284 of insertion member 222 appropriately positioned, the trigger 340 can be squeezed or depressed to translate carrying wire 220 forward relative to insertion member 222 such that one-way barb 584 engages first flexible suture anchor 50a and delivers anchor 50a on the second side 606 of the soft tissue 602 at a first location, as shown in FIGS. 19 and 21. It should be appreciated that the manner and structure of the pre-assembled anchor system 550 in-line on carrying wire 220 allows the anchor 50a to pass through a narrow opening or slit, first entry point 604, formed in the tissue 602 by the chamfered end 292 of insertion member 222. It should also be appreciated that the U-shaped trough portion 280 of insertion member 222 requires a smaller insertion area than a fully enclosed, circular shaped insertion member would require and will not core a plug of tissue.

As cam follower 234 translates carrying wire 220 forward to deploy first anchor 50a in connection with depressing trigger 340, cam follower 234 also simultaneously translates positioning member 224 forward such that distal end 306 engages second flexible anchor 50b and moves anchor 50b forward towards distal end 198 of outer cannula 86, as shown in FIGS. 19 and 20. Tubular portion 300 of positioning member 224 can have a length such that when trigger 340 is fully depressed to deploy first anchor 50a, second anchor 50b will be carried forward to a position adjacent apertures 196 and distal end 198 of outer cannula 86. In this position, retention tab 326 can engage flange 332 to retain positioning member 224 and thus anchor 50b in this advanced position when trigger 340 is released. After the first anchor 50a has been deployed, the trigger 340 can be released thereby retracting the distal end 284 of insertion member 222 such that one-way barb 584 is positioned rearward of or within bore 508 of suture anchor 50b, as generally shown in FIGS. 19 and 21. When insertion member 222 is retracting, the tail portion 548 of suture anchor 50a can engage the soft tissue side 606 such that it will be removed from insertion member 222 as insertion member 220 retracts to the stowed position.

Figure 22:
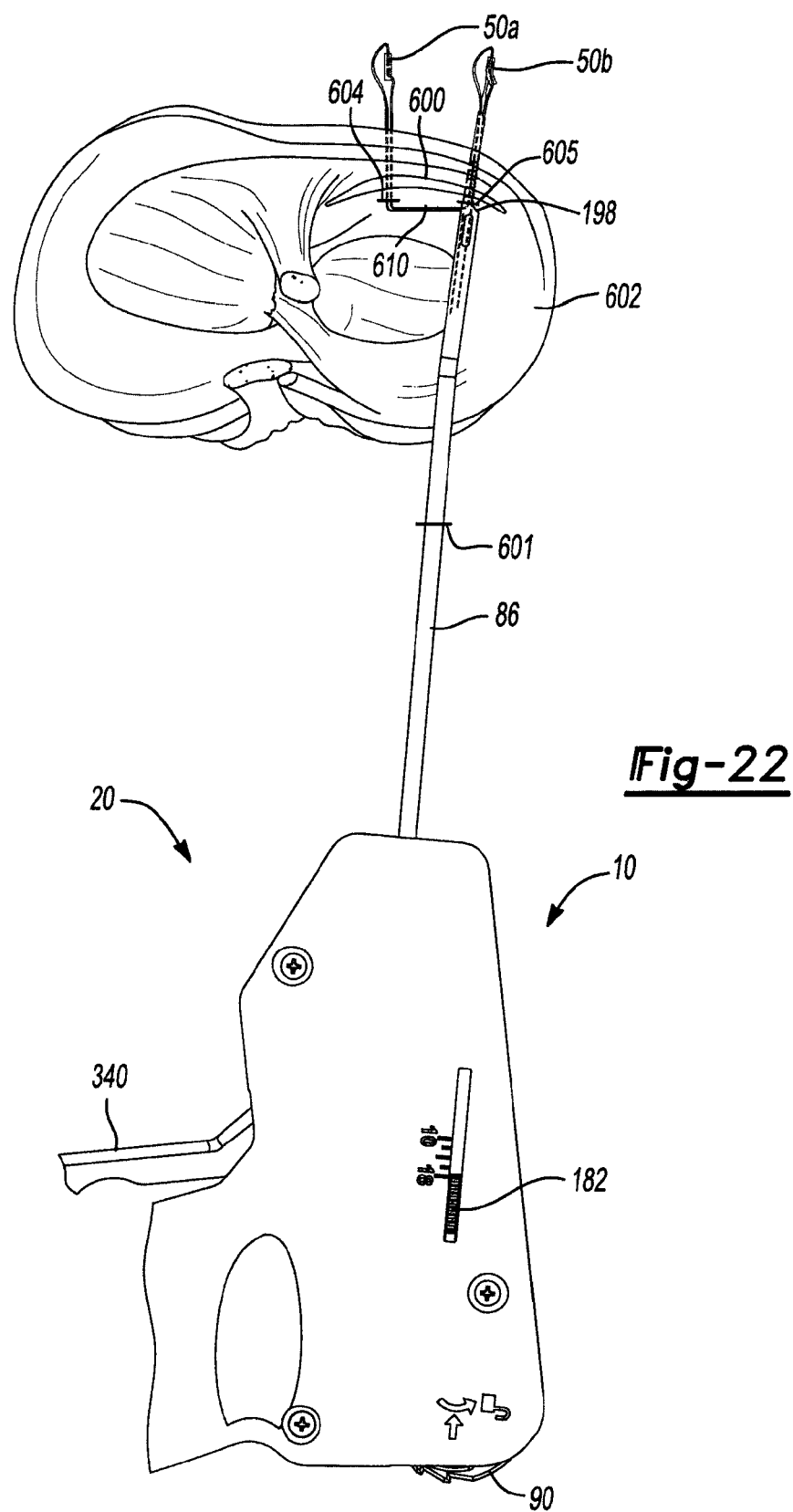
FIG. 22 is an exemplary environmental view showing first and second anchors being deployed outside of soft tissue according to the present teachings.
Figure 23:
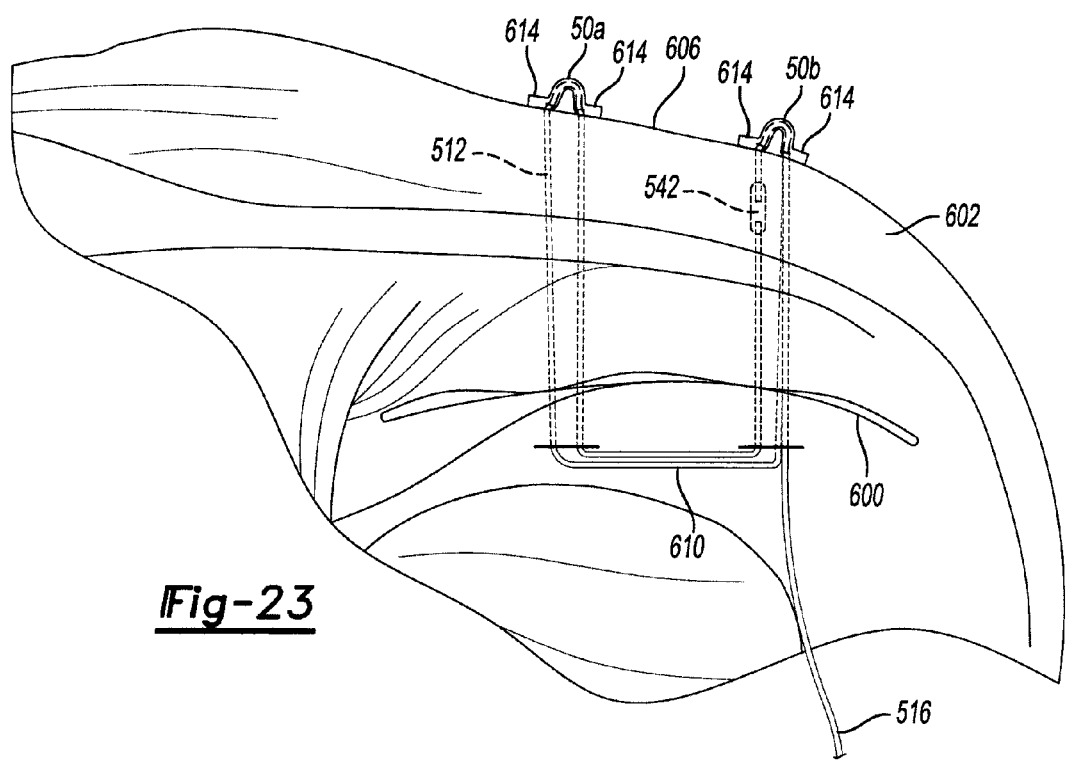
FIG. 23 is another exemplary environmental view showing first and second anchors being deployed outside of soft tissue according to the present teachings.

With the first anchor 50a deployed, the insertion device 10 can be removed from the soft tissue 602 while portions 610 of the knotless loop 546 can slide out from insertion device 10 as flexible anchor is retained in soft tissue 602. Insertion device 10 can then be inserted at a second location or entry point 605 on a second side of the soft tissue defect 600, as shown in FIG. 22. Once distal end 284 of insertion member 222 is appropriately positioned, such as beyond second side 606, trigger 340 can again be squeezed or depressed to deploy second anchor 50b adjacent to first anchor 50a. Depressing trigger 340 again translates carrying wire 220 forward such that one-way barb 584 engages an interior of bore 508 and deploys second flexible anchor 50b at the second location such that tail portion 548 of anchor 50b can engage soft tissue side 606 upon retraction on insertion member 222, as also generally shown in FIG. 22. Insertion device 10 can then be removed from the soft tissue 602 and the skin incision 601 with the second end 516 of the flexible strand 512 being removed from the soft tissue 602 along with insertion device 10, as also shown in FIG. 22. Once second anchor 50b is implanted and insertion device 10 removed from the soft tissue 602, any remaining portion of second flexible strand end 516 not removed from outer cannula 86 and housing member 560 can be subsequently removed.

Pulling the second, free end 516 of the flexible strand 512 can tighten the adjustable knotless loop 546, secure the first and second flexible anchors 50a, 50b against the second side surface 606 of the soft tissue 602, and reduce the defect 600. Further, portions 614 of the anchors 50a, 50b between the first and second ends 502, 504 and the corresponding first and second openings 528, 530, can define anchoring leg portions 614 that can provide additional resistance for securing the flexible anchors 50a, 50b on the surface 606 of the soft tissue 602, as these leg portions can be forced against surface 606 for anchoring, as shown for example in FIG. 23.

It will be appreciated from the above description and drawings that the present teachings provide flexible anchors that can be passed through tissue easily in a compact or low profile configuration and or orientation and then positioned outside tissue in a second orientation that provides anchoring without tissue penetration, preventing withdrawal from the tissue and reducing tissue injury. Further, the use of an inserter provided with preassembled anchors can help reduce the time length of the procedure and simplify manipulations required during the procedure.

It will be further understood that the various aspects of the depth positioning system, insertion system, deployment system and anchors can be mixed and matched or combined in ways other than those explicitly discussed above, without departing from the scope of the present teachings.

The foregoing discussion discloses and describes merely exemplary arrangements of the present disclosure. One skilled in the art will readily recognize from such discussion, and from the accompanying drawings and claims, that various changes, modifications and variations can be made therein without departing from the spirit and scope of the present teachings as defined in the following claims.

What is claimed is:

1. A soft tissue repair device comprising:
   a housing including a handle;
   a deployment system including an actuation member;
   an insertion system including an inserter and a slider, the slider coupled to the actuation member and movable relative to the inserter between deployed and retracted positions;
   a first anchor having a first portion and a second portion, wherein the first portion of the first anchor is carried on an external surface of the slider in a first position;
   a second anchor having a first portion and a second portion, wherein the first portion of the second anchor is carried on the external surface of the slider in a second position longitudinally spaced apart from the first anchor such that the slider extends co-axially through only the first portions of the first and second anchors and the first portions of the first and second anchors are co-axial with each other; and a flexible strand coupling the first and second anchors;
wherein the insertion system is operable to cooperate with the deployment system to move the slider from the retracted position to the deployed position to deploy the first anchor upon actuating the actuation member at a first time, and to move the slider from the retracted position to the deployed position to deploy the second anchor upon actuating the actuation member a second time after the first time.

2. The soft tissue repair device of claim 1, wherein the handle comprises a pistol grip handle and the actuation member comprises a trigger protruding from the handle and being adapted for engagement by a user.

3. The soft tissue repair device of claim 1, wherein the deployment system further comprises a cam and a cam follower, the cam coupled to the actuation member and the cam follower, the cam follower attached to the slider at a proximal end thereof, and wherein actuating the actuation member pivots the cam thereby causing the cam follower to translate the slider from the retracted position to the deployed position.

4. The soft tissue repair device of claim 3, wherein the deployment system further comprises a biasing member configured to bias the actuation member to the retracted position.

5. The soft tissue repair device of claim 3, wherein the insertion system further comprises a positioning member, the positioning member having a longitudinal axis and a through bore extending between proximal and distal ends thereof, the positioning member being slidably disposed over the slider so as to be coaxial therewith, and wherein the positioning member is positioned such that the distal end is configured to engage the second anchor and the proximal end is configured to engage the cam follower.

6. The soft tissue repair device of claim 5, wherein the slider and the positioning member are received within a through bore of the inserter, the slider and the positioning member being independently movable relative to each other and the inserter.

7. The soft tissue repair device of claim 6, wherein actuating the actuation member the first time causes the cam follower to engage and translate the positioning member such that the distal end of the positioning member engages and translates the second anchor to a third position proximate a distal end of the inserter, the positioning member including a longitudinal length such that the third position of the second anchor is adjacent to or beyond an engagement portion on a distal end of the slider when the slider is in the retracted position.

8. The soft tissue repair device of claim 7, wherein the positioning member further comprises an engagement member extending from a proximal end thereof, the engagement member configured to engage the housing upon translating the second anchor to the third position such that when the slider is translated to the retracted position, the positioning member remains stationary and maintains the second anchor in the third position.

9. The soft tissue repair device of claim 5, further comprising an outer cannula adjustably extending from the housing;
wherein the slider, positioning member and inserter are slidably received within said outer cannula, and wherein the outer cannula is coupled at a proximal end to an adjustment mechanism substantially disposed within the housing and operable to adjust a distal end of the outer cannula relative to a distal end of the inserter such that the distal end of the inserter extends a predetermined distance beyond the distal end of the outer cannula.

10. The soft tissue repair device of claim 1, wherein the insertion system further includes a depth positioning system comprising:
an outer cannula having a proximal end disposed within said housing and a distal end extending from said housing;
a translation member fixed at one end to the proximal end of said outer cannula;
a cam member coupled to the housing so as to be rotatable and translatable relative thereto, the cam member engaging a proximal end of the translating member; and
a biasing member configured to bias the translation member into engagement with the cam member;
wherein the cam member is operable to adjust a position of the distal end of the outer cannula relative to a distal end of the slider such that the distal end of the slider extends beyond the distal end of the outer cannula by one of a plurality of predetermined distances, the predetermined distances corresponding to an insertion depth of the inserter.

11. The soft tissue repair device of claim 10, wherein the cam member further comprises an outer periphery and a cam surface, the outer periphery having a toothed portion configured to engage the housing, each tooth of the toothed portion corresponding to one of the plurality of predetermined distances and being configured to maintain the outer cannula in one of the predetermined distances relative to the slider, and the cam surface being configured to cooperate with the proximal end of the translation member such that rotational motion of the cam member causes translational motion of the translating member.

12. The soft tissue repair device of claim 11, wherein the depth positioning system further comprises:
a locked position where the distal end of the outer cannula extends at least to the distal end of the inserter and the outer periphery of the cam member engages the proximal end of the translation member, and
an unlocked position where the proximal end of the translation member engages the cam surface, the cam surface being spaced apart from the outer periphery.

13. The soft tissue repair device of claim 12, wherein the actuation member further comprises a flange configured to engage a corresponding flange of the translation member such that when the depth positioning system is in the locked position the flanges engage one another and prevent the actuation member from being activated.

14. The soft tissue repair device of claim 10, wherein the cam member is disposed with the housing such that a portion of the periphery of the cam member protrudes beyond an exterior surface of the housing, the protruding portion being adapted for engagement by a user.

15. The soft tissue repair device of claim 10, wherein the cam member includes a projection extending from a central axis, and wherein the housing includes a longitudinal channel having a width substantially mating with a diameter of the projection, the channel configured to cooperate with the projection to provide for translation and rotation of the cam member relative to the housing.

16. The soft tissue repair device of claim 15, wherein the inserter further includes a second plurality of indicia indicative of a distance the distal end of the inserter extends beyond the distal end of the outer cannula, the first plurality of indicia configured to correspond to the second plurality of indicia.

17. The soft tissue repair device of claim 10, wherein the translation member further comprises a position indication member extending transverse to the translation member and protruding through an aperture on the housing, the position indication member configured to align with one of a first plurality of indicia indicative of a distance of one of the predetermined distances that the distal end of the inserter extends beyond the distal end of the outer cannula.

18. The soft tissue repair device of claim 10, wherein the distal end of the outer cannula further comprises a chamfered terminal end and an at least one aperture proximate the terminal end.

19. The soft tissue repair device of claim 1, wherein the inserter includes a tubular member defining an internal longitudinal bore extending from a proximal end towards a distal end, and a trough section having a semi-circular cross-section extending from a distal end and mating with the internal bore, the trough section carrying the first and second anchors in the respective first and second positions preloaded on the slider.

20. The soft tissue repair device of claim 19, wherein the distal end of the inserter further includes an inclined portion angled relative to a longitudinal axis of the longitudinal bore.

21. The soft tissue repair device of claim 1, wherein the slider includes an engagement portion proximate a distal end thereof, the engagement portion including a barb configured to engage the first and second anchors when the slider translates in a first direction from the retracted position to the deployed position, and slide relative to the second anchor when translating in a second, opposite direction.

22. The soft tissue repair device of claim 21, wherein the engagement portion further comprises:
a flattened area having a recess that partially defines the barb, the flattened area having a first width on a first side of the barb in a direction towards the distal end, and a second width on a second side of the slider in a direction towards the proximal end of the slider, the second width being greater than the first width.

23. The soft tissue repair device of claim 1, wherein the flexible strand passes through a portion of the first and second anchors and forms an adjustable knotless loop.

24. The soft tissue repair device of claim 23, wherein the flexible strand is a braided strand having first and second ends and defining a longitudinal passage, and wherein the knotless loop is formed by passing one of the first or second ends through a portion of the longitudinal passage of the flexible strand, and further wherein the first and second anchors are flexible sleeves formed from woven material, each flexible anchor having first and second ends and defining a longitudinal bore therethrough for receiving the slider therein.

25. The soft tissue repair device of claim 24, wherein the flexible strand passes through a portion of the longitudinal bore between first and second openings of each sleeve communicating with the bore, the first and second openings intermediate the first and second ends of each of the first and second anchors, and wherein portions of each flexible anchor between the first and second ends and the first and second openings of the corresponding anchor define leg portions.

26. A soft tissue repair device comprising: an anchor;
a housing including a pistol grip handle;
an actuation member in the form of a trigger protruding from said handle and moveable relative thereto; and
an insertion system including an inserter, a slider and a positioning member, the slider positioned coaxially within the inserter and coupled to the actuation member so as to be movable relative to the inserter between a deployed position and a retracted position upon activation of the trigger, the positioning member coaxially disposed within the inserter such that the slider extends through an internal passage of the positioning member;
wherein upon activating the trigger, the insertion system is configured to cooperate with the trigger to move the slider from the retracted position to the deployed position to deliver the anchor; wherein the anchor includes a first portion and a second portion, the first portion being carried on an external surface of the slider such that the slider extends through only the first portion and only the first portion is coaxial with the slider.

27. The soft tissue repair device of claim 26, further comprising a cam and a cam follower, the cam coupled to the trigger and including an arcuate portion having a first plurality of teeth, the cam follower fixed to a proximal end of the slider and having a second plurality of teeth in meshing engagement with the first plurality of teeth;
wherein depressing the trigger causes the cam to rotate which in turn drives the cam follower and translates the slider from the retracted position to the deployed position.

28. The soft tissue repair device of claim 26, wherein the slider includes an engagement portion proximate a distal end thereof, the engagement portion including a flattened area having a barb configured to engage the anchor when the slider translates in a first direction from the retracted position to the deployed position, and slide relative to the anchor when translating in a second, opposite direction.

29. A soft tissue repair device comprising:
a housing including a pistol grip handle;
a deployment system including an actuation member protruding from said handle and adapted for engagement by a user;
an insertion system including an inserter, a slider, and a positioning member, the inserter including a distal end extending from the housing and defining a longitudinal passage therethrough, the slider positioned coaxially within the inserter and coupled to the actuation member so as to be movable relative to the inserter between deployed and retracted positions, the positioning member coaxially disposed within the inserter such that the slider extends through an internal passage of the positioning member, the positioning member having a length less than a length of the inserter and the slider;
a depth positioning system including an outer cannula having a distal end extending from said housing and a depth adjustment mechanism, wherein at least a portion of the slider, positioning member and inserter are disposed coaxially within the outer cannula, and wherein the depth adjustment mechanism is operable to adjust a position of a distal end of the outer cannula relative to the distal end of the inserter;
a first flexible anchor having a first portion and a second portion, wherein the first portion of the first anchor is carried on an external surface of the slider in a first position on a distal side of an engagement portion of the slider;
a second flexible anchor having a first portion and a second portion, wherein the first portion of the second anchor is carried on the external surface of the slider in a second position longitudinally spaced apart from the first anchor and on a proximal side of the engagement portion such that the slider extends through only the first portions of the first and second anchors and only the first portions of the first and second anchors are co-axial with each other and the slider, wherein the positioning member includes a distal end configured to engage the second anchor; and
a flexible strand coupling the first and second anchors and forming an adjustable knotless loop;
wherein the insertion system is operable to cooperate with the deployment system to move the slider from the retracted position to the deployed position to deploy the first anchor upon actuating the actuation member at a first time, and to move the slider from the retracted position to the deployed position to have the engagement portion engage and deploy the second anchor upon actuating the actuation member a second time after the first time.

30. The soft tissue repair device of claim 29, wherein the deployment system further comprises a cam and a cam follower, the cam coupled to the actuation member and the cam follower, the cam follower attached to the slider at a proximal end thereof, wherein actuating the actuation member pivots the cam thereby causing the cam follower to translate the slider from the retracted position to the deployed position.

31. The soft tissue repair device of claim 30, wherein the positioning member further comprises a body portion at a proximal end thereof, the body portion configured to engage the cam follower when the cam follower is translated forward upon activating the actuation member the first time such that a distal end of the positioning member engages the second anchor and translates the second anchor forward to a third position, the body portion configured to engage the housing upon the cam follower being translated to the deployed position so as to prevent the second anchor from moving rearward toward a proximal end of the inserter upon retraction of the slider.

32. The soft tissue repair device of claim 29, wherein the depth positioning system further comprises:
a translation member disposed with the housing and coupled to a proximal end of the outer cannula;
a cam member having a portion disposed within said housing and a portion protruding from the housing and adapted to be engageable by a user, the cam member in cooperating engagement with a proximal end of the translation member and operable to adjust a position of the distal end of the outer cannula relative to the distal end of the inserter such that the distal end of the inserter extends beyond the distal end of the outer cannula by one of a plurality of predetermined distances.

33. The soft tissue repair device of claim 29, wherein the inserter is fixed to the housing and the slider, positioning member and outer cannula are independently moveable relative to each other and the inserter.

* * * * *